(12) United States Patent
Mak et al.

(10) Patent No.: US 9,132,138 B2
(45) Date of Patent: Sep. 15, 2015

(54) METHOD FOR THE TREATMENT OF MULTIPLE SCLEROSIS

(71) Applicant: CASI Pharmaceuticals, Inc., Rockville, MD (US)

(72) Inventors: Tak Wah Mak, Toronto (CA); Gordon Stuart Duncan, Toronto (CA)

(73) Assignee: CASI Pharmaceuticals, Inc., Rockville, MD (US)

( * ) Notice: Subject to any disclaimer, the term of this patent is extended or adjusted under 35 U.S.C. 154(b) by 0 days.

(21) Appl. No.: 13/789,849

(22) Filed: Mar. 8, 2013

(65) Prior Publication Data

US 2014/0056848 A1   Feb. 27, 2014

Related U.S. Application Data

(60) Provisional application No. 61/693,552, filed on Aug. 27, 2012.

(51) Int. Cl.
   *A61K 31/565* (2006.01)
   *A61K 45/06* (2006.01)
   *A61K 31/385* (2006.01)
   *A61K 39/00* (2006.01)
   *A61K 38/21* (2006.01)

(52) U.S. Cl.
   CPC ............. *A61K 31/565* (2013.01); *A61K 31/385* (2013.01); *A61K 38/215* (2013.01); *A61K 39/0008* (2013.01); *A61K 45/06* (2013.01)

(58) Field of Classification Search
   None
   See application file for complete search history.

(56) References Cited

PUBLICATIONS

't Hart et al., Modelling of multiple sclerosis: lessons learned in a non-human primate, Oct. 2004, Lancet Neurology 3(10): 588-597.*
Wekerle et al., Animal models of multiple sclerosis, 2006, Drug Discovery Today: Disease Models 3(4):359-367.*
Ransohoff, R. M., Animal models of multiple sclerosis: the good, the bad and the bottom line, Aug. 2012, Nature Neuroscience 15(8):1074-1077.*
Behan et al., The sad plight of multiple sclerosis research (low on fact, high on fiction): critical data to support it being a neurocristopathy, 2010, Inflammopharmacol 18:265-290.*

* cited by examiner

*Primary Examiner* — John Ulm
(74) *Attorney, Agent, or Firm* — Suzannah K. Sundby, Esq.; Canady + Lortz LLP

(57) ABSTRACT

A method for treating a subject with multiple sclerosis is disclosed herein. In one embodiment, a method is provided for treating a subject with multiple sclerosis that includes administering to the subject a therapeutically effective amount of 2ME2 or a derivative thereof.

27 Claims, 14 Drawing Sheets

METHOD FOR THE TREATMENT OF MULTIPLE SCLEROSIS

CROSS-REFERENCE TO RELATED APPLICATIONS

This application claims the benefit of U.S. Patent Application No. 61/693,552, filed 27 Aug. 2012, which is herein incorporated by reference in its entirety.

BACKGROUND OF THE INVENTION

1. Field of the Invention

This disclosure relates to the treatment of demyelinating diseases, specifically to the treatment of multiple sclerosis using 2-Methoxyestradiol (2ME2) and derivatives or analogues thereof.

2. Description of the Related Art

Multiple sclerosis (MS) is a chronic, neurological, demyelinating disease. MS can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. MS is among the most common axonal disorders in the northern hemisphere, affecting approximately 0.1% of the population, primarily young adults. The pathological hallmarks of MS include demyelination, inflammation, scarring and axonal destruction, which result in a variety of clinical symptoms including sensory loss, visual problems, muscle weakness and speech problems. Because it is not contagious, which would require U.S. physicians to report new cases, and because symptoms can be difficult to detect, the incidence of disease is only estimated and the actual number of persons with MS could be much higher.

The pathology of MS is characterized by an abnormal immune response directed against the central nervous system. In particular, T-lymphocytes are activated against the myelin sheath of the neurons of the central nervous system causing demyelination. In the demyelination process, myelin is destroyed and replaced by scars of hardened "sclerotic" tissue, known as plaque. These lesions appear in scattered locations throughout the brain, optic nerve, and spinal cord. Demyelination interferes with conduction of nerve impulses, which produces the symptoms of multiple sclerosis. Most subjects recover clinically from individual bouts of demyelination, producing the classic remitting and exacerbating course of the most common form of the disease known as relapsing-remitting multiple sclerosis.

MS develops in genetically predisposed individuals and is most likely triggered by environmental agents. The status of MS patients can be evaluated by longitudinal, monthly follow-up of magnetic resonance imaging (MRI) of the activity in the brain of MS patients. MRI offers a unique set of outcome measures in small cohorts of patients, and is thus well suited to establish data for proof of principle for novel therapeutic strategies.

There exists a need to design effective therapies that are applicable for treating a variety of immune pathologies, in both genders, with minimal side effects. The present invention satisfies this need and provides related advantages as well.

SUMMARY OF THE INVENTION

Disclosed are methods for treating a subject with a demyelinating disease, such as multiple sclerosis. The disclosed methods include administering to the subject a therapeutically effective amount of a 2ME2 or a derivative thereof. In some examples, the subject is selected that has relapsing-remitting multiple sclerosis, secondary progressive multiple sclerosis, primary progressive multiple sclerosis, or clinically isolated syndrome. In some embodiments, the methods ameliorate a symptom of multiple sclerosis such as axon damage.

In some embodiments, the subject is further administered a therapeutically effective amount of a second agent for the treatment of multiple sclerosis, such as a steroid, an anti-inflammatory compound, an immunosuppressive compound, or an antioxidant. In some example, the second agent is beta-interferon. In some example, the second agent is glatiramer acetate. In some example, the second agent is lipoic acid. In some example, the second agent is a monoclonal antibody, such as daclizumab, rituximab and natalizumab. In some example, the second agent is sanglifehrin A or a derivative of sanglifehrin A.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

DESCRIPTION OF THE DRAWINGS

This invention is further understood by reference to the drawings wherein:

FIG. 1A, Mice orally dosed with vehicle or 100 mg/kg/day Panzem NCD® (day 1 to day 30) were immunized subcutaneously (s.c.) with MOG peptide in CFA followed by intraperitoneal (i.p.) injection of PT. Disease severity was scored daily and is representative of 2 independent experiments. FIG. 1B, EAE was induced as above, but Panzem NCD® was administered at 10, 30 or 100 mg/kg. For FIGS. 1A and 1B, data shown as mean±SD for 5 mice/group, and is representative of two experiments. FIG. 1C, vehicle or Panzem NCD® was administered orally, starting at day 12 (d12) after immunization. Data shown are mean clinical scores ±SEM (n=4-5). FIG. 1D, CD4$^+$ T cells were isolated from day 12 spleens from mice treated as in FIG. 1A with vehicle or Panzem NCD®, and co-cultured with irradiated naïve splenic antigen presenting cells pulsed with MOG peptide. T cell-specific proliferation was assessed by 3H Thymidine incorporation. FIG. 3E, IFNγ and TNFα production from CD4$^+$ T cell cultures stimulated with MOG peptide, assessed by ELISA. Data shown are mean±SD for 3 mice/group. FIG. 1F, representative histopathological analyzes of CNS cross-sections from the mice at 30 days post-MOG injection. Brain sections were stained with H&E (HE), or immunostained to detect CD3 (T cells), Mac3 (activated macrophages) or GFAP (reactive astrocytes). Scale bar represents 100 μm. Arrow, hippocampus; Arrowhead, lymphocytic infiltrates; Asterix, subarachnoid space. Data shown are from one mouse per group and is representative of 3 mice/group in 2 independent experiments.

FIG. 2A, CD4$^+$ T cells were pretreated with the indicated concentrations of 2ME2 and stimulated with plate-bound anti-CD3/28 or PMA/iono. Proliferation was assayed 24 hours (left) or 48 hours (right) later by 3H-thymidine incorporation. FIG. 2B, CD4$^+$ and CD8$^+$ T cells were stimulated with anti-CD3/28 in the presence of increasing concentrations of 2ME2. CD25 expression was assessed at 6 hours or 24 hours post-stimulation by flow cytometry. FIG. 2C, Quantification of CD25 expression in purified CD4+ T cells pre-treated with increasing concentrations of 2ME2, and stimulated with anti CD3/28 or PMA/iono for 6 or 24 hours. FIG. 2D, T cells were pretreated with the indicated doses of 2ME2 and left untreated (left) or stimulated using plate-bound anti-CD3/28 (right). Viability was determined 24 hours or 48 hours post-stimulation by flow cytometry. FIG. 2E, human PBMC were activated with anti-human CD3/28 in the presence of increasing concentrations of 2ME2. Proliferation was determined 24 hours or 48 hours later by 3H-thymidine incorporation. Data are mean±SD of triplicate determinations and are representative of three separate donors. For FIG. 2A and FIG. 2E, data shown are the mean±SD of triplicate determinations, and are representative of 3 experiments. For FIG. 2B and FIG. 2C data is representative of two experiments.

FIG. 3A, T cells were pre-treated with vehicle or 2ME2 (50 µM) and stimulated with anti-CD3/28 for the indicated times. Relative expression levels of the indicated mRNAs were determined by real-time PCR. Data shown as mean±SD of duplicate determinations. FIG. 3B, T cells were pre-treated with the indicated doses of 2ME2 and left unstimulated (−), or stimulated (+) with anti-CD3/28 for 24 hours (left), or stimulated for 5 days, pre-incubated with 2ME2 and re-stimulated for 4 hours (right). Induction of IL-17 mRNA was evaluated by QRT-PCR. Data shown as mean fold increase ±SD of triplicate determinations. FIG. 3C, naïve CD4+ T cells were differentiated into Th17 cells, pre-incubated with vehicle or 2ME2 for 30 min, and stimulated for 6 hours with PMA/iono. IL-17 production in these cells was assessed by flow cytometry. Histograms show IL-17 staining in the absence (grey) and presence (black) of 50 µM 2ME2, while data values indicate % IL-17 positive cells. FIG. 3D, mice were dosed with vehicle (black bars) or 100 mg/kg 2ME2 (clear bars) for 2 days and injected with 25 µg SEB. Serum was collected at the indicated times post-SEB and levels of the indicated cytokines analyzed by ELISA. Data shown are the mean±SD of three mice per group, each individual result being derived from triplicate determinations. *$p<0.05$, $p<0.01$, *$p<0.001$.

FIG. 4A, purified T cells pre-treated with 2ME2 (50 µM) were stimulated with PMA/iono for the indicated times. Whole cell lysates were subjected to immunoblotting to detect the indicated proteins. FIG. 4B, nuclear lysates were analyzed by EMSA to detect DNA binding to NF-κB or AP-1. FP, free probe. FIG. 4C, purified T cells or B cells were pre-treated with vehicle (−) or 50 µM 2ME2 (+) and were stimulated with PMA/iono for 30 or 60 minutes (left), or with anti-CD3/28 or anti-IgM/CD40 for 24 hours (right). Nuclear fractions of lymphocytes were analyzed by immunoblotting to detect nuclear translocation of NFATc1. Lamin A, nuclear protein loading control. NS; non-specific band. For FIGS. 4A-4C, data are representative of at least two independent experiments. FIG. 4D, stably transfected NFAT and NF-κB Jurkat luciferase reporter cell lines were preincubated with 2ME2 for 30 minutes, and stimulated via crosslinking of anti-CD3/28 antibodies with goat anti-mouse antibodies (GaM). 5 hours later, secreted luciferase activity indicates relative transcriptional activity. Data is reported as normalized luciferase activity and is representative of 3 independent experiments.

DETAILED DESCRIPTION OF THE INVENTION

I. Introduction

Figure 1A:
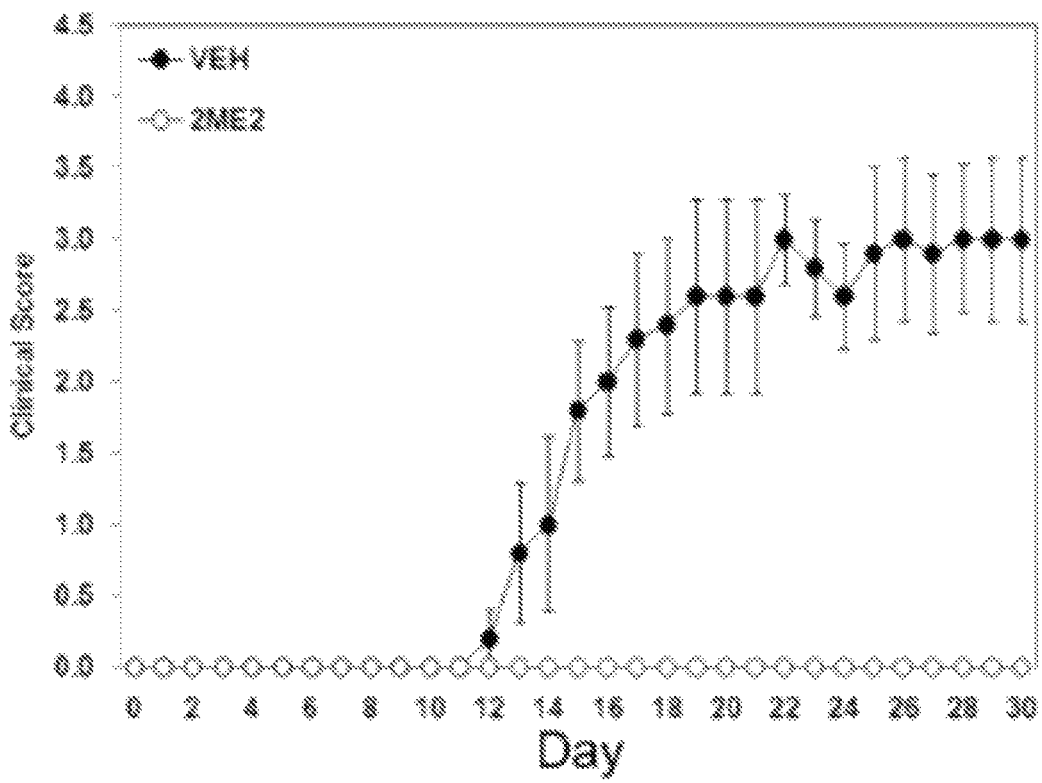
FIGS. 1A-1F show that Panzem NCD® treatment inhibits EAE.

The involvement of female sex hormones in multiple sclerosis has been proposed based on a number of clinical and experimental observations. First, a variety of diseases, including multiple sclerosis, rheumatoid arthritis and Grave's disease, preferentially affect women, and first occur during the reproductive years. During pregnancy, when levels of female sex hormones are high, clinical remissions of cell-mediated autoimmune diseases are common, with disease exacerbation often seen post-partum when sex hormone levels are low. In animal models, administration of estrogen at levels equal to or greater than those found in pregnancy has been shown to suppress the clinical and histopathological symptoms of MS.

2-Methoxyestradiol (2ME2), an endogenous metabolite of estradiol, is an anti-mitotic and anti-angiogenic cancer drug candidate. 2ME2 is an endogenous metabolite of 17β-estradiol (through metabolism of estradiol to hydroxyestradiols by CYP450, followed by methylation of hydroxyestradiols by catechol-O-methyltransferase (COMT) to form methoxyestradiols) that lacks significant estrogen receptor-binding ability. Orally active and well tolerated, 2ME2 possesses anti-proliferative, anti-angiogenic and anti-inflammatory properties and has completed phase I and II clinical trials for the treatment of a broad range of tumor types 2ME2 inhibited angiogenesis, leukocyte infiltration, local inflammation and bone resorption associated with disease, but the molecular mechanisms underlying these phenomena remain undefined. In humans, plasma levels of 2ME2 may increase up to 1000-fold during the last months of pregnancy, which intriguingly appears to correlate temporally with the remission of clinical symptoms reported in some pregnant MS and patients.

As disclosed herein 2ME2 dramatically suppresses development of murine Experimental Autoimmune Encephalomyelitis (EAE), a rodent model of multiple sclerosis (MS). 2ME2 inhibits in vitro lymphocyte activation, cytokine production and proliferation in a dose-dependent fashion. 2ME2 treatment of lymphocytes specifically reduced the nuclear translocation and transcriptional activity of Nuclear Factor of Activated T-cells (NFAT) c1, while NF-κB and AP-1 activation were not adversely affected. While not being bound by a particular theory, 2ME2 attenuates EAE through disruption of the NFAT pathway and subsequent lymphocyte activation. The findings disclosed herein provide a molecular rationale for the use of 2ME2 as a tolerable oral immunomodulatory agent for the treatment of demyelinating disorders such as MS in humans.

II. Summary of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710).

The singular terms "a," "an," and "the" include plural referents unless context clearly indicates otherwise. Similarly, the word "or" is intended to include "and" unless the context clearly indicates otherwise. The term "comprises" means "includes." In case of conflict, the present specification, including explanations of terms, will control.

To facilitate review of the various embodiments of this disclosure, the following explanations of terms are provided:

Adverse Effects: Any undesirable signs, including the clinical manifestations of abnormal laboratory results, or medical diagnoses noted by medical personnel, or symptoms reported by the subject that have worsened. Adverse events include, but are not limited to, life-threatening events, an event that prolongs hospitalization, or an event that results in medical or surgical intervention to prevent an undesirable outcome.

Ameliorating: Any observable beneficial effect of the treatment. The beneficial effect can be evidenced, for example, by a delayed onset of clinical symptoms, a reduction in severity of some or all clinical symptoms of the disease, a slower progression of the disease, a reduction in the number of relapses of the disease, an improvement in the overall health or well-being of the individual, or by other parameters well known in the art that are specific to the particular disease, such as MS. Those skilled in the art can determine, based on knowledge of the expected course of the particular disease, whether there is a delayed onset of clinical symptoms. Those skilled in the art can also determine whether there is an amelioration of the clinical symptoms following treatment as compared with before treatment or as compared to an untreated subject.

A useful method of monitoring the effect of a treatment that potentially ameliorates multiple sclerosis is magnetic resonance imaging, or MRI. As used herein, the term "magnetic resonance imaging" refers to conventional MRI methods, as well as improved magnetic resonance (MR) techniques, such as cell-specific imaging, magnetization transfer imaging (MTI), gadolinium (Gd)-enhanced MRI, proton magnetic resonance spectroscopy (MRS), diffusion-weighted imaging (DWI), functional MR imaging (fMRI), and the other neuroimaging methods known in the art. MRI methods and their applications to MS are described, for example, in Rovaris et al, *J. Neurol. Sci.* 186 Suppl 1:S3-9 (2001). MRI techniques allow an assessment of the effects of treatment on amelioration of a variety of well-known indicia of MS, including edema, blood brain barrier break-down, demyelinization, gliosis, cellular infiltration, axonal loss, T2 lesion load, T1 lesion load, gadolinium positive lesion load, and the like.

Axon damage: Axon damage includes axon degeneration and a reduction in axon density, for example in the white matter of the caudal spinal cord. White matter tissue damage includes axons undergoing Wallerian-like degeneration, reduced nerve fiber density, and demyelination. White matter tissue damage can be determined by histological examination of white matter, for example from the ventrolateral or dorsal thoracic spinal cord. White matter tissue damage may also be determined by MRI. Evidence of axonal damage can be inferred from presence of abnormal MRI signals, such as permanently decreased $T_1$ signals ("black holes"), decreased n-acetyl aspartate (NAA) and whole brain atrophy.

Axon damage also includes decreased neurofilament phosphorylation (NF-P) (see e.g., Trapp et al., *N. Engl. J. Med.* 338:278-285, 1998). Neurofilaments in myelinated axons are normally heavily phosphorylated. NF-P can be determined by immunohistochemical staining A reduction in NF-P reflects demyelination and axon damage.

Decreasing axon damage in a subject includes a reduction in white matter tissue damage as compared with an untreated subject, such as a reduction in the decrease in NF-P as compared with an untreated subject. Decreasing axon damage also encompasses preventing axon damage and repair of axon damage. Repair of axon damage in a subject includes a reduction in white matter tissue damage or a reduction in the decrease in NF-P as compared with an earlier time point.

Expanded Disability Status Scale (EDSS): A rating system that is frequently used for classifying and standardizing the condition of people with multiple sclerosis. It is also used to follow the progression of MS disability and evaluate treatment results for similar groupings of people. The EDSS score is a measure of permanent disability in MS. The score is based upon neurological testing and examination of functional systems, which are areas of the central nervous system which control bodily functions. The functional systems are: pyramidal (ability to walk), cerebellar (coordination), brain stem (speech and swallowing), sensory (touch and pain), bowel and bladder function, visual, cerebral, and other (includes any other neurological findings due to MS). The EDSS score ranges from 0 (normal neurological exam) to 10 (death due to MS). EDSS steps 1.0 to 4.5 refer to people with MS who are fully ambulatory. EDSS steps 5.0 to 9.5 are defined by the impairment to ambulation. It is possible for a subject to move in either direction on the scale, for example a worsening of symptoms or relapse is reflected in an increased EDSS score, while an improvement of symptoms or remission is reflected in a decreased EDSS score.

Experimental autoimmune encephalomyelitis (EAE): An animal model of MS (e.g., see Gold et al., *Brain* 129:1953-1971, 2006). EAE exhibits characteristic plaques of tissue injury disseminated throughout the central nervous system. Plaques show infiltration of nervous tissue by lymphocytes, plasma cells, and macrophages, which cause destruction of the myelin sheaths that surround nerve cell axons in the brain and spinal cord. EAE is induced by immunization of susceptible animals, such as mice, rats, guinea pigs, or non-human primates, with either myelin or various components of myelin. For example, EAE can be induced by immunization with components of the myelin sheath, such as myelin basic protein, proteolipid protein, or myelin oligodendrocyte glycoprotein (MOG). EAE is a useful and widely accepted model for studying mechanisms of autoimmune CNS tissue injury and for testing potential therapies for MS.

Magnetic Resonance Imaging: A noninvasive diagnostic technique that produces computerized images of internal body tissues and is based on nuclear magnetic resonance of atoms within the body induced by the application of radio waves.

Brain MRI is a tool for understanding the dynamic pathology of multiple sclerosis. $T_2$-weighted brain MRI defines lesions with high sensitivity in multiple sclerosis and is used as a measure of disease burden. However, such high sensitivity occurs at the expense of specificity, as $T_2$ signal changes can reflect areas of edema, demyelination, gliosis and axonal loss. Areas of gadolinium (Gd) enhancement demonstrated on $T_1$-weighted brain MRI are believed to reflect underlying blood-brain barrier disruption from active perivascular inflammation.

Such areas of enhancement are transient, typically lasting <1 month. Gadolinium-enhanced $T_2$-weighted brain MRI is therefore used to assess disease activity. Most $T_2$-weighted ($T_2$) lesions in the central white matter of subjects with multiple sclerosis begin with a variable period of $T_1$-weighted ($T_1$) gadolinium (Gd) enhancement and that $T_1$ Gd-enhancing and $T_2$ lesions represent stages of a single pathological process. The brain MRI techniques for assessing $T_1$ and $T_2$ Gd-enhancing lesions are standard (e.g., see Lee et al., *Brain* 122 (Pt 7):1211-2, 1999).

Multiple sclerosis: A disease classically described as a central nervous system white matter disorder disseminated in time and space that presents as relapsing-remitting illness in 80-85% of patients. Diagnosis can be made by brain and spinal cord MRI, analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on $T_2$-weighted and fluid attenuated inversion recovery images, gadolinium enhancement of active lesions, hypointensive "black holes" (representing gliosis and axonal pathology), and brain atrophy on $T_1$-weighted studies. Serial MRI studies can be used to indicate disease progression.

Relapsing-remitting multiple sclerosis is a clinical course of MS that is characterized by clearly defined, acute attacks with full or partial recovery and no disease progression between attacks.

Secondary-progressive multiple sclerosis is a clinical course of MS that initially is relapsing-remitting, and then becomes progressive at a variable rate, possibly with an occasional relapse and minor remission.

Primary progressive multiple sclerosis presents initially in the progressive form.

Pharmaceutical agent or drug: A chemical compound or composition capable of inducing a desired therapeutic or prophylactic effect when properly administered to a subject.

Pharmaceutical agent or drug: A chemical compound capable of inducing a desired therapeutic or prophylactic effect when properly administered to a subject.

Pharmaceutically acceptable carriers: The pharmaceutically acceptable carriers useful in the methods disclosed herein are conventional. *Remington's Pharmaceutical Sciences*, by E. W. Martin, Mack Publishing Co., Easton, Pa., 19th Edition (1995), describes compositions and formulations suitable for pharmaceutical delivery of 2ME2 and derivatives herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain non-toxic auxiliary substances, such as wetting or emulsifying agents, preservatives, salts, amino acids, and pH buffering agents and the like, for example sodium or potassium chloride or phosphate, Tween, sodium acetate or sorbitan monolaurate.

Purified: The term purified does not require absolute purity or isolation; rather, it is intended as a relative term. For pharmaceuticals, such as 2ME2 or a derivative thereof, "substantial" purity of 90%, 95%, 98% or even 99% or higher of the active agent can be utilized.

Subject: A human or non-human animal. In one embodiment, the subject has or is suspected of having multiple sclerosis. In some embodiments a subject is selected that has or is suspected of having multiple sclerosis. A subject who has multiple sclerosis who has failed a therapeutic protocol (such as administration of interferon-beta) is a subject who does not respond or fails to respond adequately to the therapy, such that their condition has not improved sufficiently, not changed, or deteriorated in response to treatment with a therapeutically effective amount of the drug. A subject who has failed a therapeutic protocol can require escalating doses of the drug to achieve a desired effect.

In one example, the failure of a subject with MS to respond to a therapeutic agent, such as interferon-beta, can be measured as a recurrence of Gd-contrasting MRI lesions to at least half of the mean of the baseline monthly contrasting lesions over six months. In other examples, a subject with MS that fails to respond to a therapeutic agent, such as interferon-beta treatment, is identified by the subject experiencing one or more exacerbations in an 18 month period of interferon-beta therapy, exhibiting an increase of 1 point or more on the EDSS over 18 months of treatment, or having persistence or reoccurrence of contrast enhancing lesions on brain MRI scans to at least one-half the mean of a baseline of monthly contrast enhancing lesions established over a 6-month baseline period measured prior to the beginning of the interferon-beta therapy.

Symptom and sign: Any subjective evidence of disease or of a subject's condition, i.e., such evidence as perceived by the subject; a noticeable change in a subject's condition indicative of some bodily or mental state. A "sign" is any abnormality indicative of disease, discoverable on examination or assessment of a subject. A sign is generally an objective indication of disease. Signs include, but are not limited to any measurable parameters such as tests for immunological status or the presence of lesions in a subject with multiple sclerosis.

Therapeutically effective amount: A dose sufficient to prevent advancement, or to cause regression of the disease, or which is capable of reducing symptoms caused by the disease, such as multiple sclerosis.

III. Description of Several Embodiments

Disclosed herein are methods for treating, demyelinating diseases, such as multiple sclerosis (MS). Methods are provided herein for the treatment of subjects that have MS or are suspected of having MS. In one embodiment the subject has relapsing-remitting multiple sclerosis. In other embodiments, the methods disclosed are used for the treatment of subjects with other forms of multiple sclerosis, such as secondary or primary progressive multiple sclerosis. In several examples, the subject has failed prior therapy with a therapeutic agent. For example, the subject may have been treated with an interferon-beta or another anti-inflammatory agent, but did not respond to this therapy. The disclosed methods include administering to a subject, such as a human subject, for example a human subject having or suspected of having a demyelinating disease, such as MS, a composition that includes a therapeutic amount of 2-ME2, or a derivative thereof. In some embodiments, a subject that has or is suspected of having MS is selected for treatment. In some embodiments, the subject is administered a therapeutically effective amount of a compound having the formula:

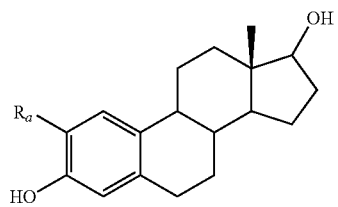

wherein $R_a$ is selected from —OCH$_3$, —OCH$_2$CH$_3$, —CH$_3$, —CH$_2$CH$_3$, —CCCH$_3$, —CHCH—CH$_3$, or —CH$_2$—CHCH$_2$.

Other derivatives of 2ME2 which can be used in the disclosed methods include those disclosed in International Patent Publication No. WO 2008/094665; U.S. Pat. Nos. 8,158,612 and 5,504,074; U.S. patent application Ser. No. 09/641,327, filed Aug. 18, 2000; U.S. patent application Ser. No. 09/779,331, filed Feb. 8, 2001; U.S. patent application Ser. No. 09/933,894, filed Aug. 21, 2001; U.S. patent application Ser. No. 09/939,208, filed Aug. 24, 2001; U.S. patent application Ser. No. 10/789,471, filed Feb. 27, 2004; U.S. patent application Ser. No. 10/856,340, filed May 28, 2004; U.S. patent application Ser. No. 11/077,977, filed on Mar. 11, 2005; and U.S. patent application Ser. No. 11/489,263 filed Jul. 19, 2006, which are specifically incorporated herein by reference in their entirety. Thus, in some embodiments, one or more of the compounds disclosed in International Patent Publication No. WO 2008/094665; U.S. Pat. Nos. 8,158,612 and 5,504,074; U.S. patent application Ser. No. 09/641,327, filed Aug. 18, 2000; U.S. patent application Ser. No. 09/779,331, filed Feb. 8, 2001; U.S. patent application Ser. No. 09/933,894, filed Aug. 21, 2001; U.S. patent application Ser. No. 09/939,208, filed Aug. 24, 2001; U.S. patent application Ser. No. 10/789,471, filed Feb. 27, 2004; U.S. patent application Ser. No. 10/856,340, filed May 28, 2004; U.S. patent application Ser. No. 11/077,977, filed on Mar. 11, 2005; and U.S. patent application Ser. No. 11/489,263 filed Jul. 19, 2006, are administered to a subject, such as a subject with MS.

The compositions described herein can be provided as physiologically acceptable formulations using known techniques, and the formulations can be administered by standard routes. In general, the compounds can be administered by topical, oral, rectal or parenteral (e.g., intravenous, subcutaneous or intramuscular) route. In addition, the compositions can be incorporated into polymers allowing for sustained release, the polymers being implanted in the vicinity of where delivery is desired, or the polymers can be implanted, for example, subcutaneously or intramuscularly or delivered intravenously or intraperitoneally to result in systemic delivery of the compounds.

The formulations can be administered in the form of a tablet, a capsule, a lozenge, a cachet, a solution, a suspension, an emulsion, a powder, an aerosol, a suppository, a spray, a pastille, an ointment, a cream, a paste, a foam, a gel, a tampon, a pessary, a granule, a bolus, a mouthwash, or a transdermal patch.

The formulations include those suitable for oral, rectal, nasal, inhalation, topical (including dermal, transdermal, buccal and sublingual), vaginal, parenteral (including subcutaneous, intramuscular, intravenous, intradermal, intraocular, intratracheal, and epidural) or inhalation administration. The formulations can conveniently be presented in unit dosage form and can be prepared by conventional pharmaceutical techniques. Such techniques include the step of bringing into association the active ingredient and a pharmaceutical carrier(s) or excipient(s). In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil emulsion, etc.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface-active or dispersing agent. Molded tablets may be made by molding, in a suitable machine, a mixture of the powdered compound moistened with an inert liquid diluent. The tablets may optionally be coated or scored and may be formulated so as to provide a slow or controlled release of the active ingredient therein.

Formulations suitable for topical administration in the mouth include lozenges comprising the ingredients in a flavored base, usually sucrose and acacia or tragacanth; pastilles comprising the active ingredient in an inert base such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered in a pharmaceutical acceptable carrier. In one embodiment the topical delivery system is a transdermal patch containing the ingredient to be administered.

Formulations for rectal administration may be presented as a suppository with a suitable base comprising, for example, cocoa butter or a salicylate.

Formulations suitable for nasal administration, wherein the carrier is a solid, include a coarse powder having a particle size, for example, in the range of 20 to 500 microns which is administered in the manner in which snuff is taken; i.e., by rapid inhalation through the nasal passage from a container of the powder held close up to the nose. Suitable formulations, wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing, in addition to the active ingredient, ingredients such as carriers as are known in the art to be appropriate.

Formulation suitable for inhalation may be presented as mists, dusts, powders or spray formulations containing, in addition to the active ingredient, ingredients such as carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for parenteral and or oral administration also include, but are not limited to, nanoparticle formulations made by numerous methods as disclosed in U.S. patent application Ser. No. 10/392,403 (Publication No. US 2004/0033267), U.S. patent application Ser. No. 10/412,669 (Publication No. US 2003/0219490), U.S. Pat. No. 5,494,683, U.S. patent application Ser. No. 10/878,623 (Publication No. US 2005/0008707), U.S. Pat. No. 5,510,118, U.S. Pat. No. 5,524,270, U.S. Pat. No. 5,145,684, U.S. Pat. No. 5,399,363, U.S. Pat. No. 5,518,187, U.S. Pat. No. 5,862,999, U.S. Pat. No. 5,718,388, and U.S. Pat. No. 6,267,989, all of which are hereby incorporated herein by reference in their entirety. A review of drug formulation technology is provided in "Water Insoluble Drug Formulation" by Rong Liu, editor, pp. 1-633, (2000) CRC Press LLC, which is incorporated herein by reference in its entirety.

By forming nanoparticles, the compositions disclosed herein are shown to have increased bioavailability. The particles of the compounds of the present invention have an effective average particle size of less than about 2 microns, less than about 1900 nm, less than about 1800 nm, less than about 1700 nm, less than about 1600 nm, less than about 1500 nm, less than about 1400 nm, less than about 1300 nm, less than about 1200 nm, less than about 1100 nm, less than about 1000 nm, less than about 900 nm, less than about 800 run, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods well known to those of ordinary skill in the art. It is understood that the particle sizes are average particle sizes and the actual particle sizes will vary in any particular formulation. Often, surface stabilizers are used to form stable nanoparticles; however, this method of forming nanoparticles is only one of many different methods of forming effective nanoparticle compositions. The formulations may be presented in unit-dose or multi-dose containers, for example, sealed ampules and vials, and may be stored in freeze-dried (lyophilized) conditions requiring only the addition of a sterile liquid carrier, for example, water for injections, immediately prior to use. Extemporaneous injection solutions and suspensions may be prepared from sterile powders, granules and tablets of the kinds previously described.

It should be understood that, in addition to the ingredients particularly mentioned above, the formulations of the present invention may include other agents conventional in the art having regard to the type of formulation in question, for example, those suitable for oral administration may include flavoring agents, and nanoparticle formulations (e.g.; less than 2000 nanometers, preferably less than 1000 nanometers, most preferably less than 500 nanometers in average cross section) may include one or more than one excipient chosen to prevent particle agglomeration.

Generally, it is desirable to prepare the compositions as pharmaceutical compositions appropriate for the intended application. Accordingly, methods for making a medicament or pharmaceutical composition containing the polypeptides, nucleic acids, adenovirus vectors or adenoviruses described above are included herein. Typically, preparation of a pharmaceutical composition (medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow for uptake of nucleic acids or virus by target cells.

Therapeutic compositions can be provided as parenteral compositions, such as for injection or infusion. Such compositions are formulated generally by mixing a disclosed therapeutic agent at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, a disclosed therapeutic agent can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of 2ME2 or a derivative thereof dispersed (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Administration of therapeutic compositions can be by any common route as long as the target tissue (typically, the respiratory tract) is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers or other excipients.

The pharmaceutical compositions can also be administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain about 100 mg of human serum albumin per milliliter of phosphate buffered saline. Other pharmaceutically acceptable carriers include aqueous solutions, non-toxic excipients, including salts, preservatives, buffers and the like may be used. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components of the pharmaceutical composition are adjusted according to well-known parameters.

Additional formulations are suitable for oral administration. Oral formulations can include excipients such as, pharmaceutical grades of mannitol, lactose, starch, magnesium stearate, sodium saccharine, cellulose, magnesium carbonate and the like. Exemplary formulations can be found in U.S. Patent publication No. 20020031527, the disclosure of which is incorporated herein by reference. When the route is topical, the form may be a cream, ointment, salve or spray. Exemplary methods for intramuscular, intranasal and topical administration of the adenovirus vectors and adenoviruses described herein can be found, for example, in U.S. Pat. No. 6,716,823, which is incorporated herein by reference.

An effective amount of the pharmaceutical composition is determined based on the intended goal, for example vaccination of a human or non-human subject. The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes nucleic acids or viruses.

An appropriate effective amount can be readily determined by one of skill in the art. Such an amount will fall in a relatively broad range that can be determined through routine trials, for example within a range of about 10 µg to about 1 mg. However, doses above and below this range may also be found effective.

Therapeutic compositions that include a disclosed therapeutic agent can be delivered by way of a pump (see Langer, supra; Sefton, *CRC Crit. Ref Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semi-permeable polymer matrices in the form of shaped articles, for example films, or microcapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983, poly(2-hydroxyethyl methacrylate)); (Langer et al., *J. Biomed. Mater. Res.* 15:167-277, 1981; Langer, *Chem. Tech.* 12:98-105, 1982, ethylene vinyl acetate (Langer et al., Id.) or poly-D-(−)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Deliver*); Systems, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

The pharmaceutical composition may also comprise one or more agent or drug as known to be therapeutically active in the treatment of multiple sclerosis. In a further embodiment these agents may be selected from the group consisting of steroid, anti-inflammatory compound, immunosuppressive compound, and antioxidant compound. The pharmaceutical composition may also be administered orally. Additional routes of administration may include sublingual, transdermal, transmucosal, or rectal (e.g., suppository or enema form).

Methods for preparing pharmaceutical compositions are known to those skilled in the art (see *Remington's Pharmaceutical Science,* 19th ed., Mack Publishing Company, Easton, Pa., 1995). Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate.

Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical compositions for oral use can be formulated, for example, as tablets, troches, lozenges, aqueous or oily suspensions, dispersible powders or granules, emulsion hard or soft capsules, or syrups or elixirs. Such compositions can be prepared according to standard methods known to the art for the manufacture of pharmaceutical compositions and may contain one or more agents selected from the group of sweetening agents, flavoring agents, coloring agents and preserving agents in order to provide pharmaceutically elegant and palatable preparations. Tablets contain the active ingredient in admixture with suitable non-toxic pharmaceutically acceptable excipients including, for example, inert diluents, such as calcium carbonate, sodium carbonate, lactose, calcium phosphate or sodium phosphate; granulating and disintegrating agents, such as corn starch, or alginic acid; binding agents, such as starch, gelatin or acacia, and lubricating agents, such as magnesium stearate, stearic acid or talc. The tablets can be uncoated, or they may be coated by known techniques in order to delay disintegration and absorption in the gastrointestinal tract and thereby provide a sustained action over a longer period. For example, a time delay material such as glyceryl monostearate or glyceryl distearate may be employed. Pharmaceutical compositions for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium such as peanut oil, liquid paraffin or olive oil.

Pharmaceutical compositions can include pharmaceutically acceptable salts of the disclosed compounds. Pharmaceutically acceptable salts of the presently disclosed compounds include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. Pharmaceutically acceptable salts are also inclusive of the free acid, base, and zwitterionic forms. Description of suitable pharmaceutically acceptable salts can be found I in *Handbook of Pharmaceutical Salts, Properties, Selection and Use*, Wiley VCH (2002).

2ME2 and derivatives thereof can be administered for therapeutic treatment of a subject with multiple sclerosis. Thus, a therapeutically effective amount of a composition comprising 2ME2 or a derivative thereof is administered to a subject already suffering from MS, in an amount sufficient to improve a sign or a symptom of the disorder. Single or multiple administrations of the composition can be carried out with dose levels and pattern being selected by a practitioner such as physician. Generally, multiple doses are administered. In a particular example, the composition is administered parenterally once per day. However, the composition can be administered twice per day, three times per day, four times per day, six times per day, every other day, twice a week, weekly, or monthly. Treatment will typically continue for at least a month, more often for two or three months, sometimes for six months or a year, and may even continue indefinitely, i.e., chronically. Repeat courses of treatment are also possible.

2ME2 or derivatives thereof can be administered in combination with a therapeutically effective amount of at least one other agent for the treatment of MS. For example, 2ME2 or derivatives thereof can be administered with a therapeutically effective amount of a monoclonal antibody, such as daclizumab (ZENAPAX®, U.S. Pat. No. 5,530,101, incorporated herein by reference), natalizumab (TYSABRI®), rituximab (RITUXIN®) or alemtuzumab (CAMPATH®, U.S. Pat. No. 5,545,403). In a further example, the additional agent is an anti-inflammatory agent, such as glatiramer acetate. In an additional example, the additional agent is an anti-oxidant, such as lipoic acid. In another example, the additional agent is a non-cyclosporin inhibitor of cyclophilin D, such as sanglifehrin A or derivatives of sanglifehrin A which have cyclophilin D inhibitory activity (Clarke et al. *J. Biol. Chem.* 277: 34793-34799, 2002). Additional agents also include, but are not limited to, glatiramer acetate (COPAXONE®), inosine, corticosteroids such as prednisone or methylprednisolone; immunosuppressive agents such as cyclosporin (or other calcineurin inhibitors, such as PROGRAF®), azathioprine, sirolimus (RAPAMUNE®), mycophenolate mofetil (CELLCEPT®), laquinimod (ABR-215062), and fingolimod (FTY720); anti-metabolites such as methotrexate; and antineoplastic agents such as mitoxantrone. A further additional agent is a combination vaccine against the T cell receptor peptides BV5S2, BV6S5, and BV 13S1 (NEUROVAX®, Darlington *Curr. Opin. Mol. Ther.* 7:598-603, 2005).

In several embodiments, a therapeutically effective amount of 2ME2 or a derivative thereof and a therapeutically effective amount of interferon beta are administered to a subject with MS. The interferon-beta can be interferon-beta-1a, interferon-beta-1b or a combination thereof. If the interferon-beta is interferon-beta 1b (e.g., BETASERON®), an exemplary dose is 0.25 mg by subcutaneous injection every other day. However, higher or lower doses can be used, for example from 0.006 mg to 2 mg daily, biweekly, weekly, bimonthly or monthly. If the interferon-beta is interferon-beta 1a and is AVONEX®, an exemplary dose is 30 μg injected intramuscularly once a week. However, higher or lower doses could be used, for example 15 to 75 μg daily, biweekly, weekly, bimonthly or monthly. If the interferon-beta 1a is REBIF®, an exemplary dose is 44 μg three times per week by subcutaneous injection. However, higher or lower doses can be used, including treatment daily, biweekly, weekly, bimonthly, or monthly. Additionally, the dosage may be changed during the course of therapy. For example, REBIF® can be administered at an initial dose of 8.8 μg for the first two weeks, then 22 μg for the next two weeks, and then at 44 μg for the rest of the therapy period. In specific embodiments, AVONEX® can be administered at a dose of 30 μg per week or BETASERON® can be administered at a dose of 0.25 mg every other day.

Administration of interferon-beta also can be performed on strict or adjustable schedules. For example, interferon-beta is administered once weekly, every-other-day, or on an adjustable schedule, for example based on concentration in a subject. One of skill in that art will realize that the particular administration schedule will depend on the subject and the dosage being used. The administration schedule can also be different for individual subjects or change during the course of the therapy depending on the subject's reaction. In specific examples, interferon-beta 1a is administered every other week, or monthly.

The combined administration of 2ME2 or a derivative thereof and interferon-beta includes administering interferon-beta either sequentially with 2ME2 or derivatives thereof, e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

The combined administration of 2ME2 or a derivative thereof and additional pharmaceutical agents includes administering the additional agent either sequentially with 2ME2 or a derivative thereof, e.g., the treatment with one agent first and then the second agent, or administering both agents at substantially the same time, e.g., an overlap in performing the administration. With sequential administration a subject is exposed to the agents at different times so long as some amount of the first agent remains in the subject (or has a therapeutic effect) when the other agent is administered. The treatment with both agents at the same time can be in the same dose, e.g., physically mixed, or in separate doses administered at the same time.

In several examples, 2ME2 or a derivative thereof is administered to a subject with relapsing-remitting MS, primary progressive MS, or secondary progressive MS. In a particular example, 2ME2 or a derivative thereof is administered to a subject during a relapse phase, for example to promote recovery. In a non-limiting example, 2ME2 or a derivative thereof is administered in combination with an anti-inflammatory agent, such as glatiramer acetate.

Treatment with 2ME2 or a derivative thereof, alone or in combination with other agents, will reduce the severity of disease. In one example, the severity of the disease is reduced by at least about 25%, such as about 50%, about 75%, or about 90% reduction. In another example, treatment with 2ME2 or a derivative thereof will reduce white matter tissue damage by at least about 30%, such as about 40%, about 50%, about 70%, or about 80%. In a further example, treatment with 2ME2 or a derivative thereof will reduce axon loss by at least about 30%, such as about 50%, about 60%, about 70%, or about 80%. In another example, treatment with 2ME2 or a derivative thereof will promote repair of axon damage by at least about 25% improvement, such as about 30%, about 40%, or about 50% improvement.

Treatment with 2ME2 or a derivative thereof, alone or in combination with other agents, will decrease MRI measures of MS. In several embodiments, the administration of 2ME2 or a derivative thereof results in stabilization of the number of black holes on an MRI and/or stabilization of the number of $T_2$-weighted lesions and/or an increase in NAA following administration of 2ME2 or a derivative thereof. In one example, the number of $T_2$-weighted lesions will decrease by at least about 10%, such as about 20%, about 30%, about 50% or about 70%. In a further example, treatment with 2ME2 or a derivative thereof will decrease $T_1$-weighted hypointense regions. In a particular example, the $T_1$ hypointense regions will decrease in number by at least about 10%, such as about 20%, about 30%, about 50% or about 70%. In an additional particular example, the $T_1$ hypointense regions will decrease in volume by at least about 10%, such as about 20%, about 30%, about 50% or about 70%. In another example, NAA levels will increase by at least about 10%, such as about 20%, about 30%, or about 40%.

In several embodiments, treatment with 2ME2 or a derivative thereof, alone or in combination with other agents, will reduce the average number of MS exacerbations per subject in a given period (such as 6, 12, 18 or 24 months) by at least about 25%, such as at least about 40% or at least about 50%, as compared to a control. In one embodiment, the number of MS exacerbations is reduced by at least about 80%, such as at least about 90%, as compared to control subjects. The control subjects can be untreated subjects or subjects not receiving 2ME2 or a derivative thereof (e.g., subjects receiving other agents).

Treatment with 2ME2 or a derivative thereof, alone or in combination with other agents, can also reduce the average rate of increase in the subject's disability score over some period (e.g., 6, 12, 18 or 24 months), e.g., as measured by the EDSS score, by at least about 10% or about 20%, such as by at least about 30%, 40% or 50%. In one embodiment, the reduction in the average rate of increase in the EDSS score is at least about 60%, at least about 75%, or at least about 90% compared to control subjects, such as untreated subjects or subjects not receiving 2ME2 or a derivative thereof but possibly receiving other agents. In another embodiment, treatment with 2ME2 or a derivative thereof will prevent decline in the subject's EDSS score. In a further embodiment, the subject's EDSS score will improve, by at least about 10% or about 20%, such as by at least about 30%, 40% or 50% compared to control subjects, such as untreated subjects or subjects not receiving 2ME2 or a derivative thereof but possibly receiving other agents. These benefits can be demonstrated in one or more randomized, placebo-controlled, double-blinded, Phase II or III clinical trials and will be statistically significant (e.g., $p<0.05$).

The disclosed methods are further illustrated by the following non-limiting examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention.

EXAMPLES

Materials and Methods

Mice.

For all mice experiments C57/BL6 mice were used (Jackson Labs).

EAE.

Mice were dosed p.o. via a feeding needle with 10-100 mg/kg 2ME2 (Panzem® NCD) or vehicle (water) at day 1 to day 30 or from day 12 to day 30. For EAE induction, Mice were s.c. immunized with 115 µg MOG 35-55 peptide (Washington Biotech) emulsified in Complete Freund's Adjuvant (CFA; Difco) supplemented with 400 µg/mL *Mycobacterium tuberculosis* (Difco). On days 0 and 2 post-immunization, mice were i.p. injected with 300 ng pertussis toxin (List Biological). Clinical signs of EAE were monitored daily according to the following criteria: 0, no disease; 1, decreased tail tone; 2, hind limb weakness or partial paralysis; 3, complete hind limb paralysis; 4, front and hind limb paralysis; 5, moribund state. Mice were sacrificed when they reached an EAE disease score of 4, and these animals were assigned a score of 5 for the rest of observation period for the purposes of calculating the mean EAE disease score. At the end of the 30 day observation period, any surviving mice were sacrificed and their brains subjected to histological analyzes.

Histology and Immunohistochemistry.

Brains were obtained from mice at 30 days post-MOG injection and fixed in 10% buffered formalin for several days. Fixed brains were cut into about 1.5 mm thick coronal sections and paraffin-embedded according to standard laboratory procedures. For histological and immunohistochemical assessments, 5 μm thick paraffin sections were cut and stained with hematoxylin and eosin (H&E) or analyzed by immunohistochemistry according to standard laboratory procedures. For immunohistochemical staining, the following Abs and dilutions were used: anti-CD3 (Dako, 1:200), anti-B220 (BD Pharmingen, 1:3000), anti-Mac3 (BD Pharmingen, 1:100), and anti-GFAP (Dako, 1:2000).

Lymphocyte Purification.

All lymphocyte subsets were purified to >95% using the I-Mag magnetic bead separation system (BD).

Drug Treatment In Vitro.

Cells were pre-incubated with various concentrations of 2ME2 (Entremed) or vehicle (DMSO) for 30 minutes at 37° C.

Lymphocyte Activation, Proliferation and Viability.

Purified CD4+ T cells were stimulated with plate-bound anti-CD3 (clone 2C11, BD, 10 ng/ml) plus anti-CD28 (clone 37.51, BD, 100 ng/ml). Purified B220+ B cells were stimulated with anti-IgM (Jackson, 5 μg/ml), anti-CD40 (clone 3/20, BD, 5 μg/ml) or LPS (Sigma, 20 μg/ml) for the times indicated in FIG. 3. CD25 and CD69 expression was determined by flow cytometry (FACSCanto II, BD) and analyzed using FloJo software (Treestar Inc). Proliferation was assessed by 3H-thymidine incorporation. Viability and upregulation of cell surface markers on activated T cells were assessed by flow cytometry using Annexin V and propridium iodide. Human Peripheral blood mononuclear cells (PBMC) were isolated using Mono-Poly Resolving Medium (MP Biomedical) according to the manufacturer's protocols and activated with anti-CD3 (clone UCHT1) and anti-CD28 (clone CD28.2).

Quantitative Real Time PCR.

Total mRNA and cDNAs were prepared from stimulated T cells and cDNAs added to a Low Density TaqMan® array (TLDA, ABI) according to manufacturer's instructions. Fold increase for mRNAs was determined by normalising against the expression of GAPDH. For IL-17 mRNA, quantitative RT-PCR was performed using Sybr Green (Invitrogen) and fold increase was determined by normalising against 18S rRNA.

CD4+ T Helper (Th) Cell Purification and Differentiation Conditions.

For in vitro Th cell differentiation assays, naïve CD4+ CD62L+ Th cells were isolated from spleens and LN and sorted using a magnetic bead cell purification kit according to the manufacturer's instructions (Miltenyi). For priming, enriched Th cells were stimulated for 72 hours with 1 μg/mL anti-CD3 (BD Biosciences) and 1 μg/mL anti-CD28 (BD Biosciences) Abs. For differentiation of Th17 cells, primed Th cells received 5 μg/mL anti-IFNγ, 30 ng/mL rmIL-6 (Peprotech) 2 ng/mL rhTGF-β (R&D) and 50 U rhIL-2. For analysis of cytokines by intracellular staining, T cells harvested after culture in vitro were washed twice with HBSS and preincubated with the indicated concentrations of 2ME2 for 30 minutes before stimulation for 6 hours with 50 nM PMA plus 750 nM ionomycin in the presence of Golgi Plug (BD; 1:1000). Stimulated T cells were washed once in PBS containing 2% fetal bovine serum (FBS). Permeabilization and intracellular cytokine staining were performed using Cytofix/Cytoperm kits (BD Biosciences; IL-17A, IFNγ) according to each manufacturer's instructions. Flow cytometry was performed on a Canto II instrument (BD Biosciences) and analyzed using FlowJo 7.5 software (Tree Star).

Staphylococcal Enterotoxin B (SEB).

Mice were dosed i.p. for 3 days with 100 mg/kg 2ME2 (Panzem® NCD) or vehicle, then injected i.p. with 25 μg SEB (Sigma). Serum cytokine levels were assessed with the Cytometric Bead Array (CBA, BD) according to manufacturer's instructions. Statistical significance was calculated using Student's t test.

GPER1 Dependence.

Purified C57/BL6 CD4+ T cells were preincubated with the GPER1 antagonist G15 (100 nM, Tocris) and 2ME2 (0-50 μM), or the GPER1 agonist G1 (1-100 nM, Tocris) for 30 minutes, and activated with plate bound anti-CD3 plus soluble anti-CD28. 6 hours later, cells were harvested, stained with anti-CD4 and anti-CD25. CD25 expression was monitored on a HTS FACSCanto II (BD) and analyzed with FloJo (Treestar Inc).

Biochemical Dissection of Signaling Pathways.

Whole cell lysates of stimulated T cells were immunoblotted with Ab recognizing phospho-protein kinase B (AKT) (Ser473), phospho-JNK (Thr183/Tyr185, p46 and p54 Clone G9, antibody "2"), phospho-ERK (Thr202/Tyr204) or phospho-IκBα (Ser32) (NEB); phospho-JNK (Thr183/Tyr185, p54 pSAPK/JNK, clone G7, antibody "1") or IκBα(C21) (Santa Cruz); β-tubulin (Millipore) or actin (Sigma). Infrared dye-labeled secondary Ab (anti-rabbit Alexa fluor 680, Invitrogen, and anti-mouse IR800, LICOR) were visualized with the Odyssey® scanner (LICOR).

EMSA.

Nuclear extracts of T cells stimulated with PMA (10 ng/ml)+calcium ionophore A23187 (iono, Sigma) (50 ng/ml) for 30 or 60 minutes were prepared according to a standard protocol. These extracts were subjected to EMSA using infrared dye end-labeled DNA oligonucleotides (LICOR) specific for NF-κB and AP-1 and a protocol specified by the manufacturer. Complexes were visualized on the Odyssey® scanner (LICOR).

NFATc Analysis.

T or B cells pre-incubated with vehicle or 2ME2 (50 μM) were stimulated with PMA (10 ng/ml)+iono (50 ng/ml); plate-bound anti-CD3 (30 ng/ml)+anti-CD28 (100 ng/ml); or anti-IgM (1 μg/ml)+anti-CD40 (1 μg/ml). Nuclear extracts (5 μg protein) were immunoblotted with anti-NFATc1 (clone 7A6, Santa Cruz) and anti-Lamin A (clone H-102, Santa Cruz).

Gaussia Luciferase Assays.

Luciferase Assays were performed using Jurkat cells harboring a stably integrated Gaussia-luciferase reporter gene under the control of NF-κB or NFAT binding sites (Termed NFAT/NF-κB-GLuc reporter Jurkat). Gaussia luciferase contains a secretion peptide sequence mediating quantitative secretion of active enzyme into the surrounding medium. 1.5×10⁵ GLuc reporter cells were stimulated in 96 well plates for 5 hours. For each sample, 20 μl of supernatant was subjected to a Gaussia luciferase assay (p.j.k). Luciferase activity was measured in 96-well plates using a Orion L microplate Luminometer (Berthold Detection Systems) with an integration time of 3.0 seconds. In parallel, cell viability was determined using the CellTiter-Glo® Luminescent Cell Viability Assay (Promega) and normalized Gluc activity was calculated as the ratio between Gluc activity and cell viability counts.

Statistical Methods.

Where appropriate, all differences were evaluated using the two-tailed Student's t-test as calculated using Excel (Microsoft) software. Data are presented as the mean±SEM.

Results

As disclosed herein 2ME2 inhibits development of EAE in mice. 2ME2 has been reported to display anti-inflammatory properties in collagen-induced arthritis (CIA), an autoimmune model of RA dependent on T cell activation, and at least partly driven by Th17 cells. Given the importance of T cell activation and the development of encephalitogenic Th17 cells in orchestrating the inflammatory destruction of myelin in EAE, the therapeutic potential of 2ME2 was investigated in this autoimmune disease model.

Figure 1B:
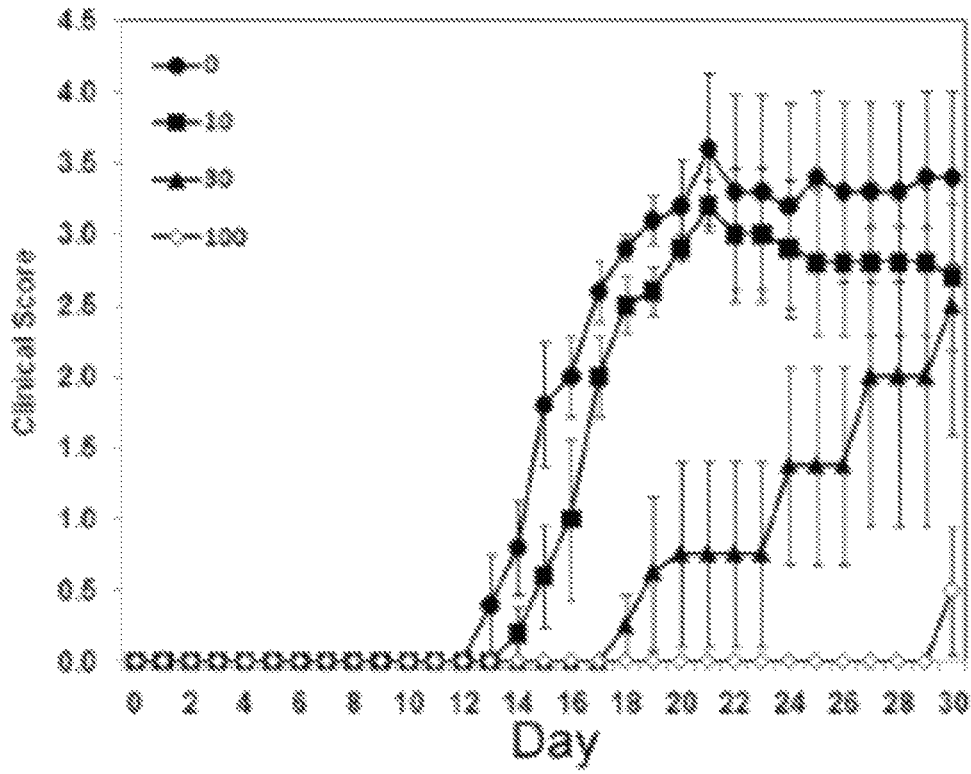

Subcutaneous (s.c.) immunization with MOG35-55 in complete Freund's adjuvant (CFA), together with injection of petussis toxin (PT), resulted in induction of EAE in all vehicle-treated mice. Disease kinetics in these mice was consistent (onset at day 12 to day 14), and all mice developed severe disease by day 30 (FIG. 1A). In striking contrast, mice dosed orally throughout the course of the experiment (day 1 through day 30) with 100 mg/kg Panzem NCD® (a NanoCrystal® dispersion formulation of 2ME2 that increases bioavailability) were completely resistant to EAE, and developed no clinical manifestations of EAE by day 30 (FIG. 1A). This inhibition of EAE was dose-dependent, with doses of 10, 30 and 100 mg/kg producing progressively greater reductions in clinical score (FIG. 1B).

Figure 1C:
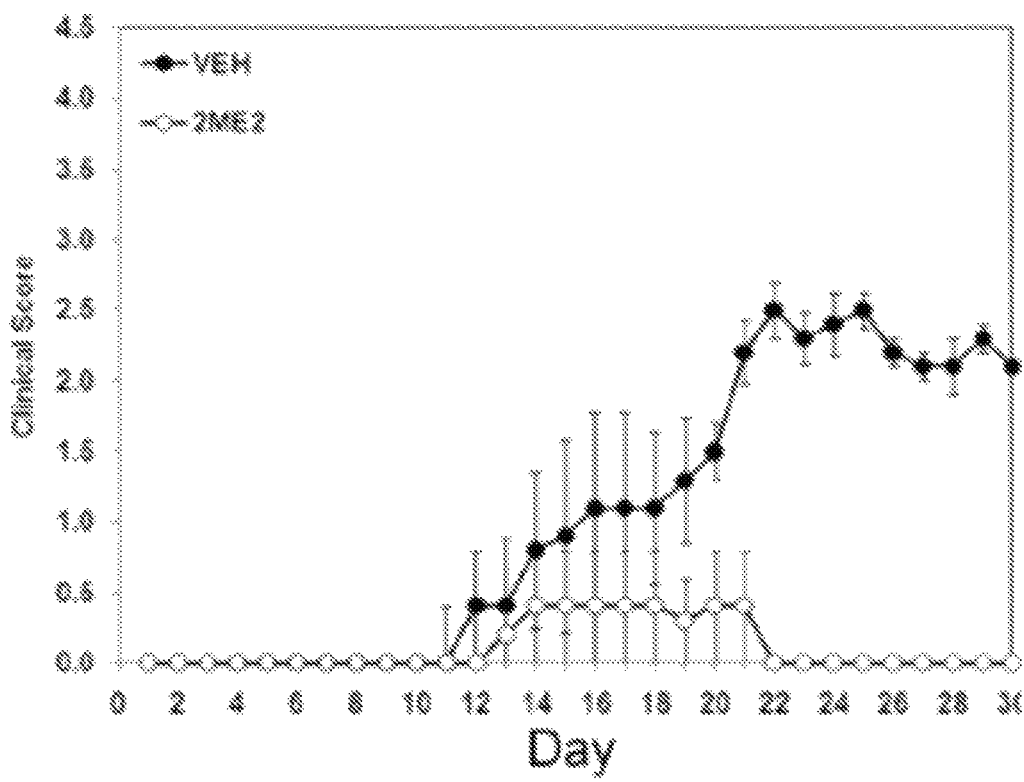

The dramatic nature of EAE inhibition by Panzem NCD® when given throughout the disease course prompted the examination of the ability of 2ME2 to reverse or inhibit disease when mice were treated after the initiation phase of EAE. Mice were thus dosed with either vehicle or 100 mg/kg Panzem NCD® at day 12 after MOG peptide immunization just as disease symptoms should become apparent, and disease course was monitored daily. Only 1/5 Panzem NCD® treated mice developed very mild, transient disease, whereas 4/4 vehicle treated mice developed EAE by day 30 (FIG. 1C). 2ME2 can therefore inhibit development of disease even when the initiation and priming phase of EAE has already occurred.

Figure 1D:
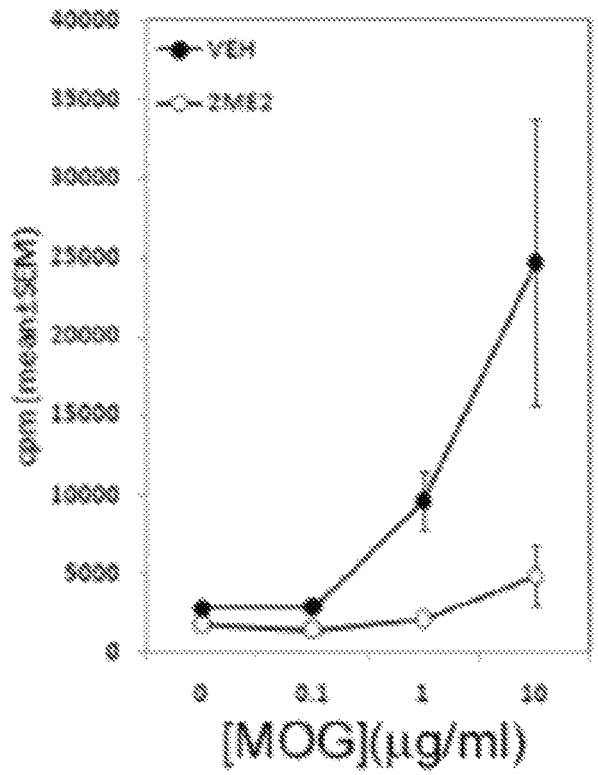
Figure 1E:
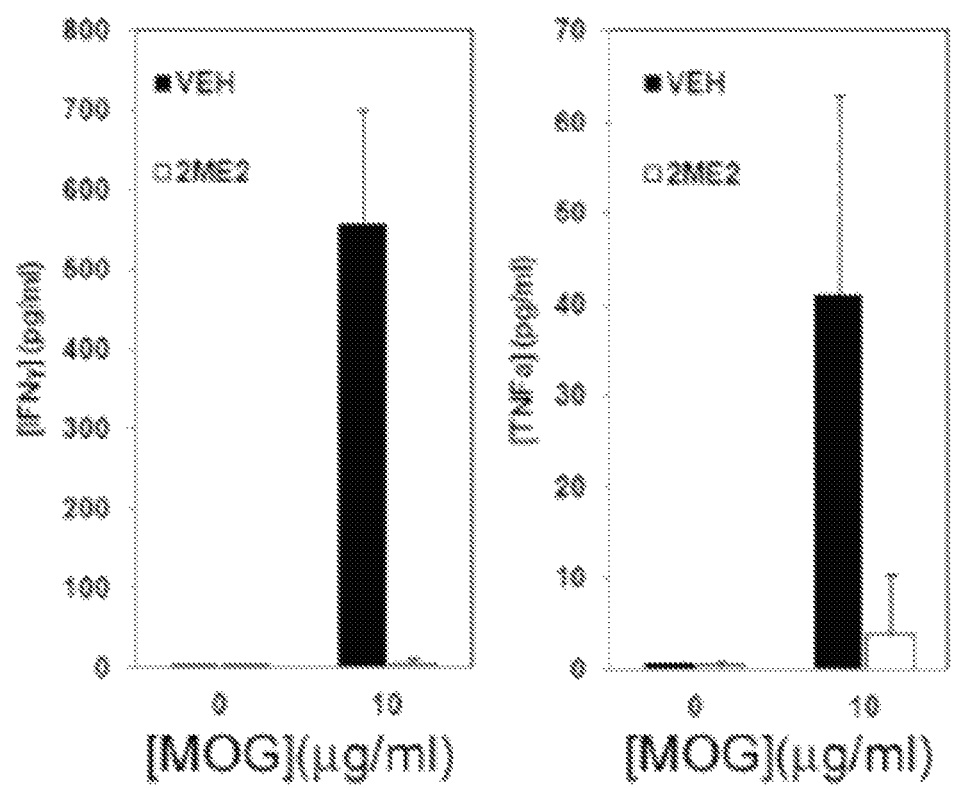

EAE is a T cell dependent disease. To assay for the presence of MOG-reactive T cells in Panzem NCD® treated (dosed from d-1) mice, CD4$^+$ T cells were isolated from spleens of vehicle or drug treated (from day 0) mice at day 12 post immunization with MOG peptide. Co-culture of these CD4$^+$ T cells with irradiated naïve splenic antigen presenting cells pulsed with MOG peptide revealed a severe defect in antigen-specific CD4$^+$ T cell proliferation in T cells from Panzem-treated mice (FIG. 1D), together with a dramatic reduction in MOG-dependent IFNγ and TNFα production (FIG. 1E). These results show that Panzem NCD® effectively curtails the early production and expansion of Ag-specific T cells in this disease model.

Figure 1F:
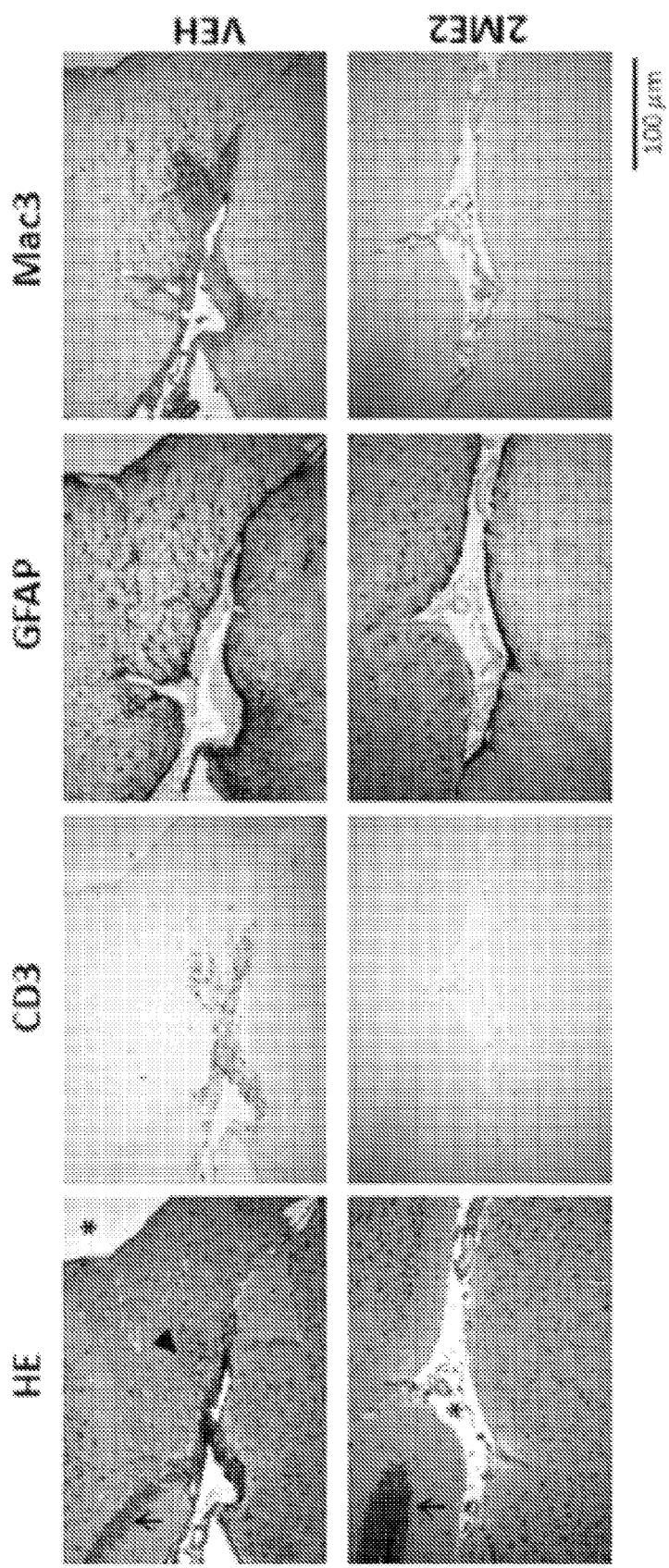

Histopathological analyzes of brain tissue 30 days after MOG immunization revealed dense immune cell infiltrates in the cerebrum of vehicle treated mice (FIG. 1F, H&E panel). Immunohistochemical staining indicated a perivascularly-centered, diffuse, wide-spread infiltrate of CD3$^+$ T cells which was absent in Panzem NCD®-treated animals (FIG. 1F, CD3). The recruitment of bone marrow-derived myeloid cells has been shown to be crucial for development of EAE. Accordingly, extensive perivascular macrophage activation was apparent in vehicle-treated mice, although activated macrophage staining was dramatically reduced in Panzem-treated mice (FIG. 1F, Mac3). Moreover, whereas vehicle-treated mice showed large numbers of reactive GFAP$^+$ astrocytes within the infiltrated areas (a sign of severe CNS inflammation), a reduction in the number of reactive astrocytes were detectable in the Panzem NCD®-treated group (FIG. 1F, GFAP). Taken together, these results show that 2ME2 inhibits EAE in a dose-dependent manner by blunting the recruitment of inflammatory cells to the CNS.

Figure 2A:
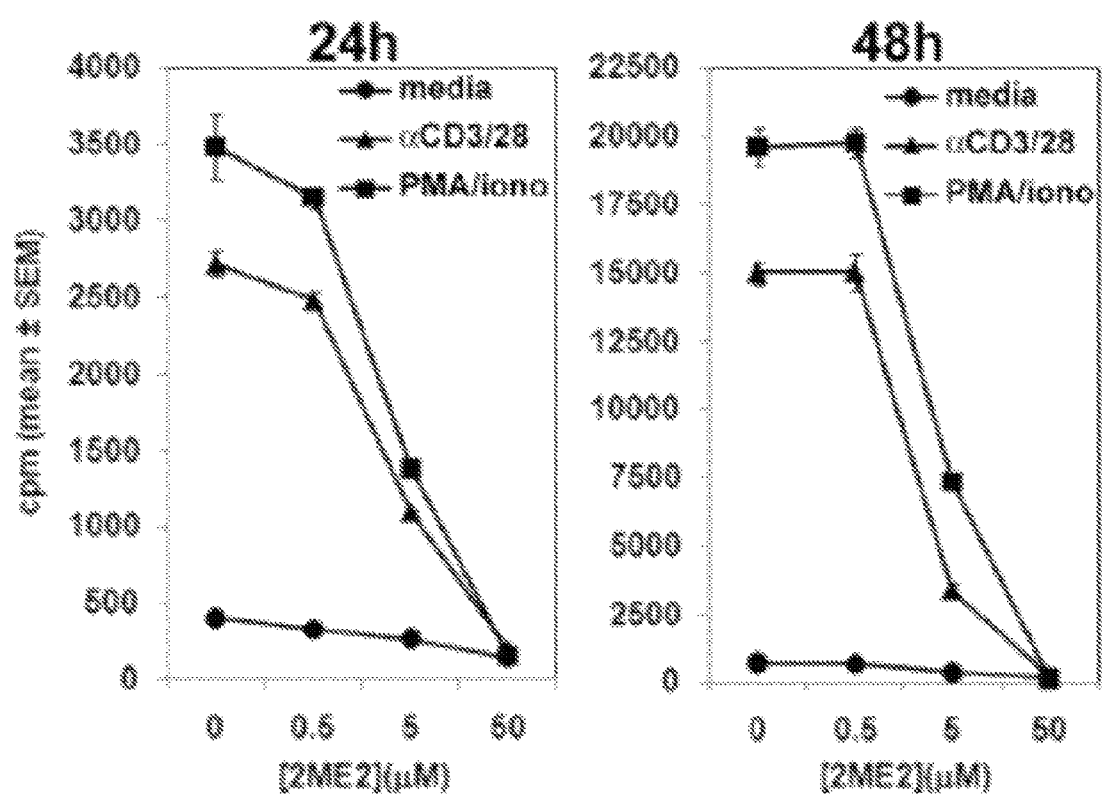
FIGS. 2A-2E, show proliferation and activation of T cells are inhibited by 2ME2.
Figure 2B:
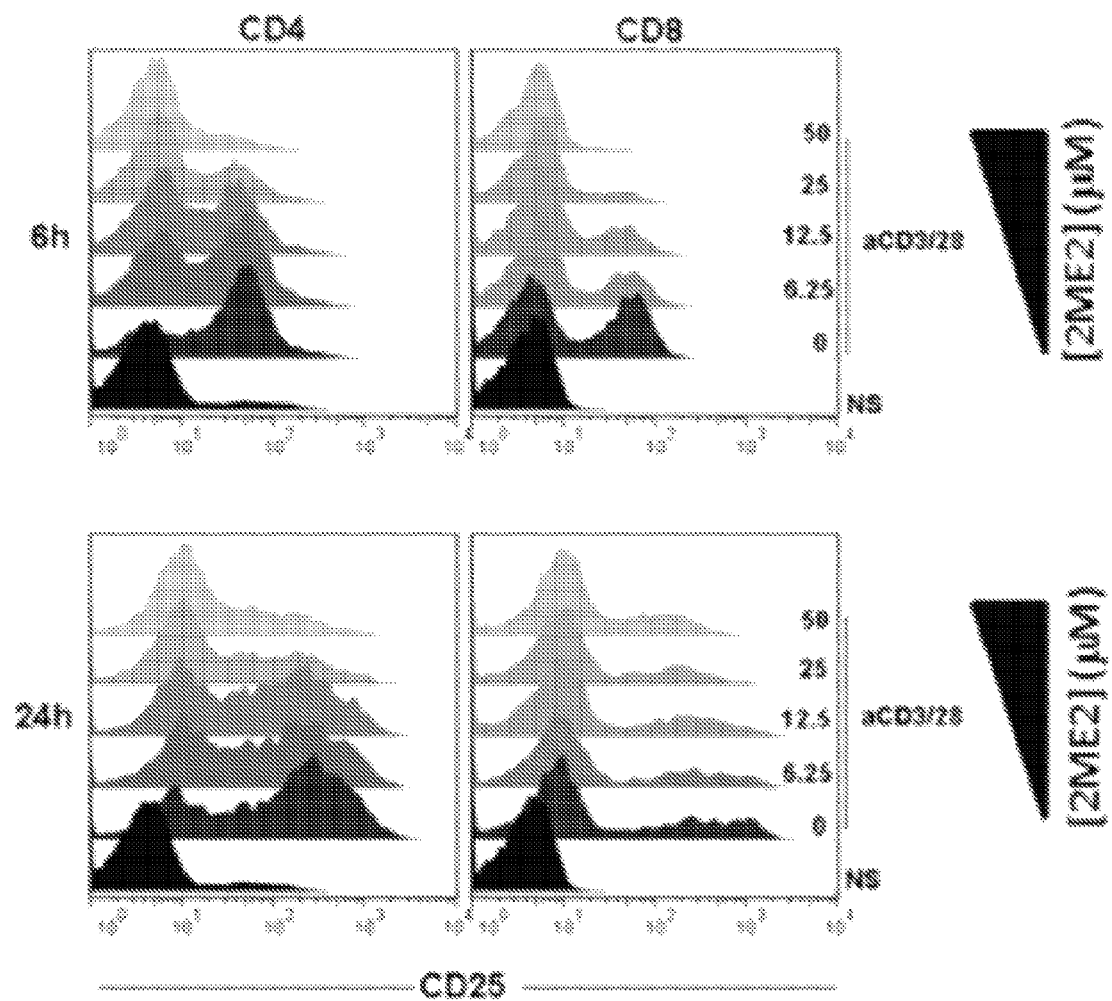
Figure 2C:
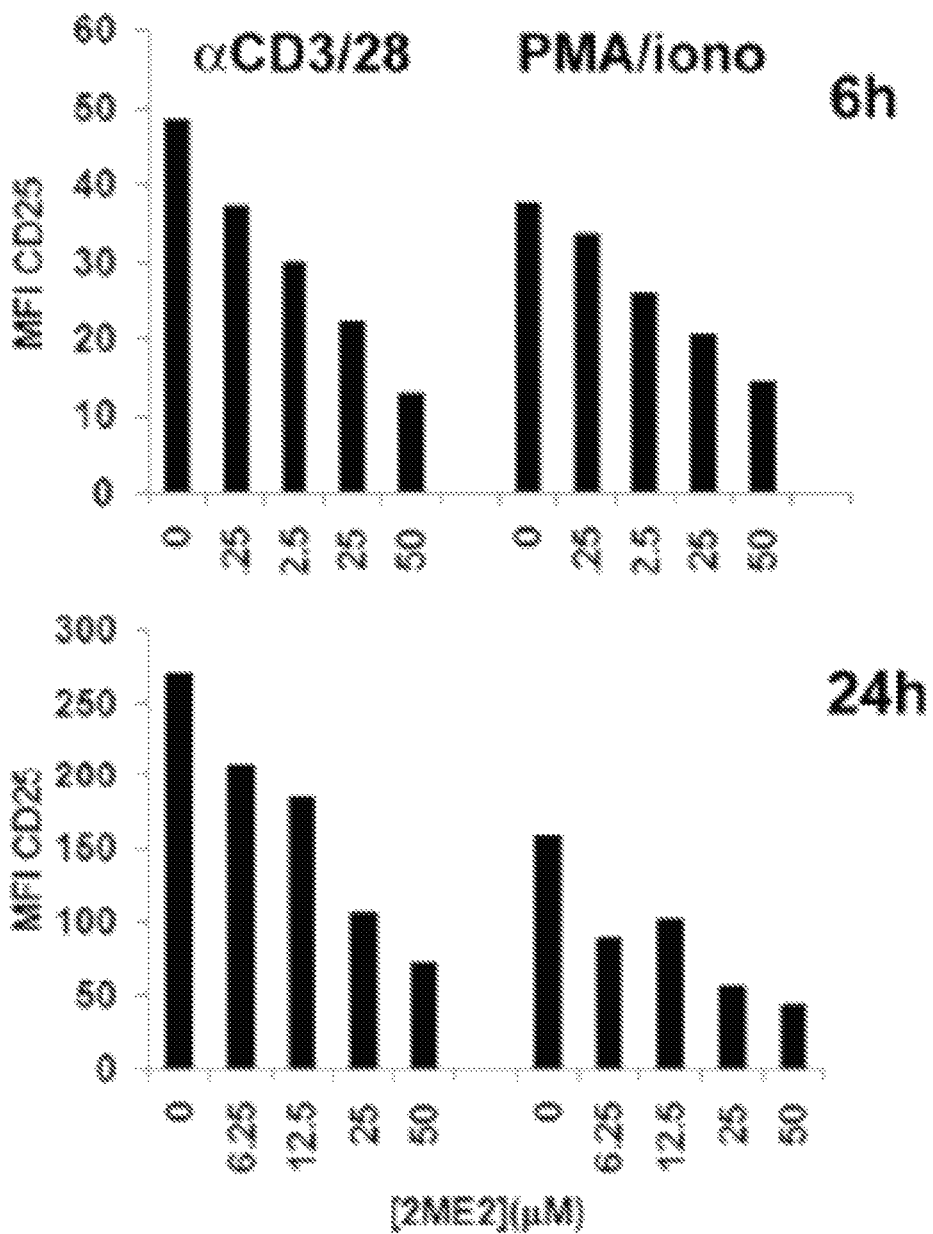
Figure 2D:
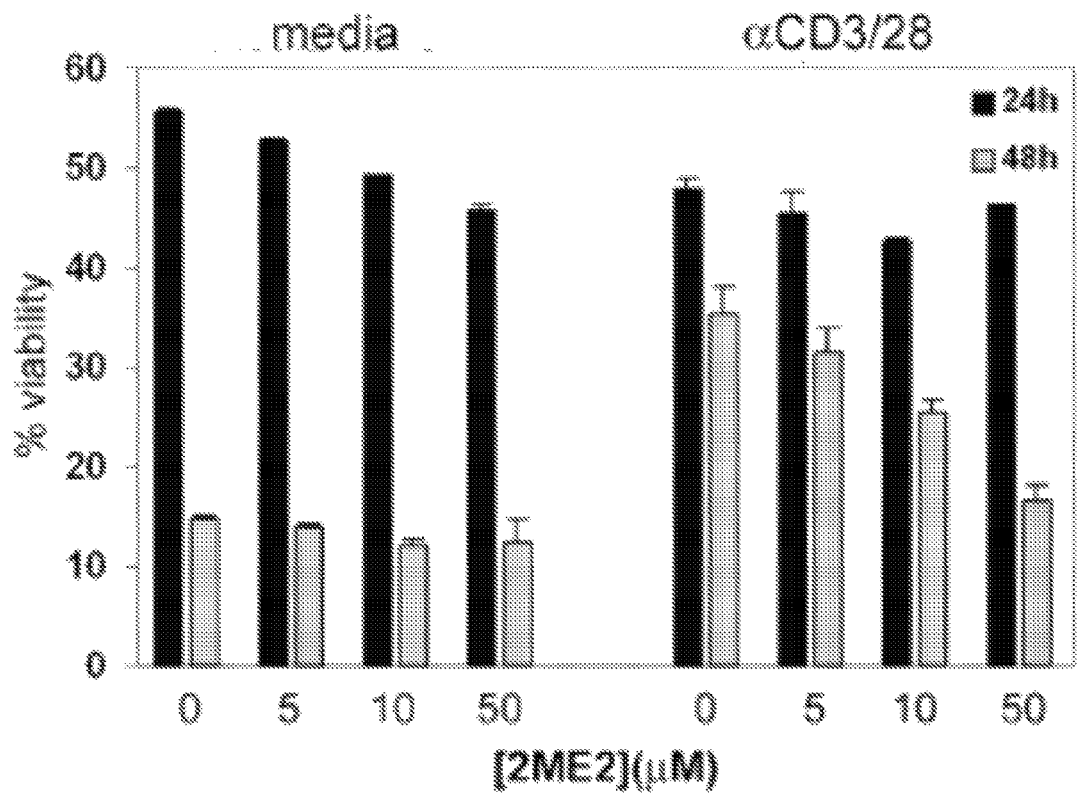

2ME2 inhibits T and B cell proliferation and activation. To investigate the effects of 2ME2 on T cell activation directly, purified CD4$^+$ T cells were pre-treated with 2ME2 or vehicle and proliferation measured by 3H-thymidine incorporation at 24 hours or 48 hours post-T cell Receptor (TCR) stimulation. 2ME2 caused a dose-dependent inhibition of anti-CD3/28 or phorbol myristate acetate (PMA)+calcium ionophore (iono)-dependent proliferation (FIG. 2A). 2ME2 also blocked up-regulation of the early T cell activation markers CD25 (FIGS. 2B and 2C) and CD69, irrespective of whether T cells were stimulated with anti-CD3/28 or PMA/iono. This inhibition of activation and proliferation at 24 hours by 2ME2 was not due to induction of cell death because only a modest 2ME2-dependent increase in apoptosis was observed in un-stimulated 2ME2-treated T cells at 24 hours, while none was apparent in activated 2ME2-treated T cells (FIG. 2D). At 48 hours post-stimulation however, 2ME2-treated activated T cells showed reduced viability, presumably due to a 2ME2-dependent defect in activation.

Figure 5:
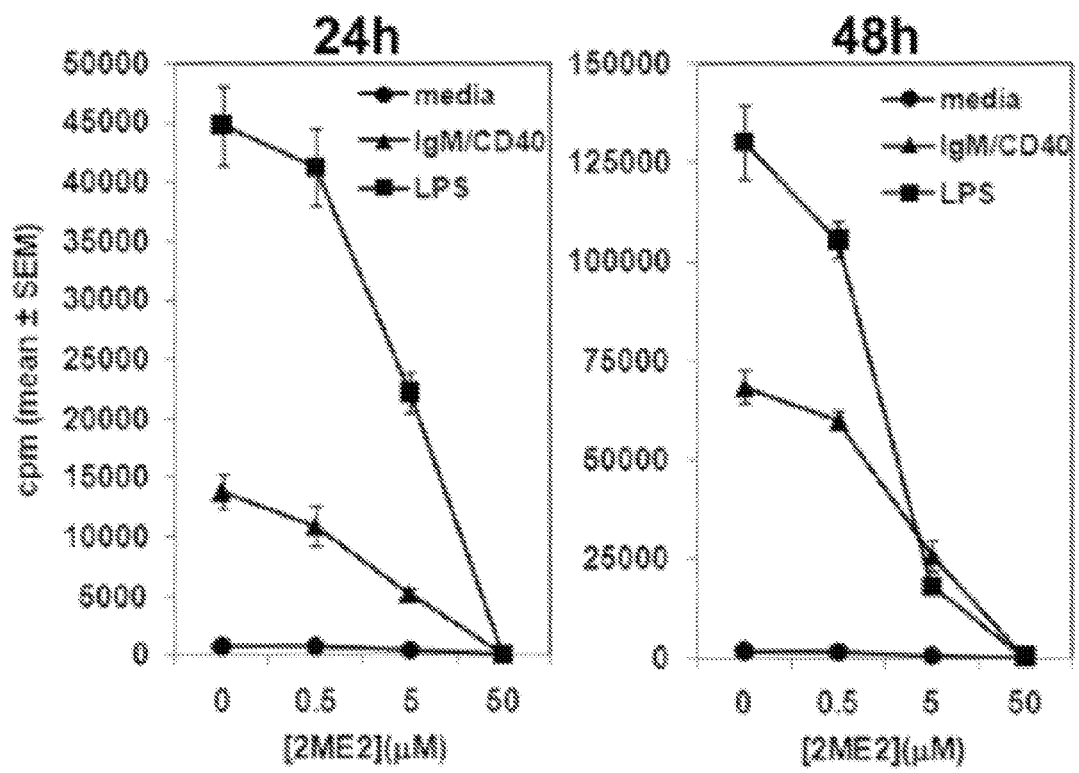
FIG. 5 shows splenic B-cells that were pretreated with the indicated doses of 2ME2 and stimulated as indicated. Proliferation was assayed after 24 hours (left) or 24 hours (right) by 3H-thymidine incorporation.

2ME2 had a similar inhibitory effect on the proliferation of purified splenic B cells, regardless of whether they were stimulated with soluble anti-IgM, anti-IgM/CD40, or LPS (FIG. 5). The up-regulation of CD25 and CD69 observed in activated B cells was also prevented by 2ME2.

Figure 2E:
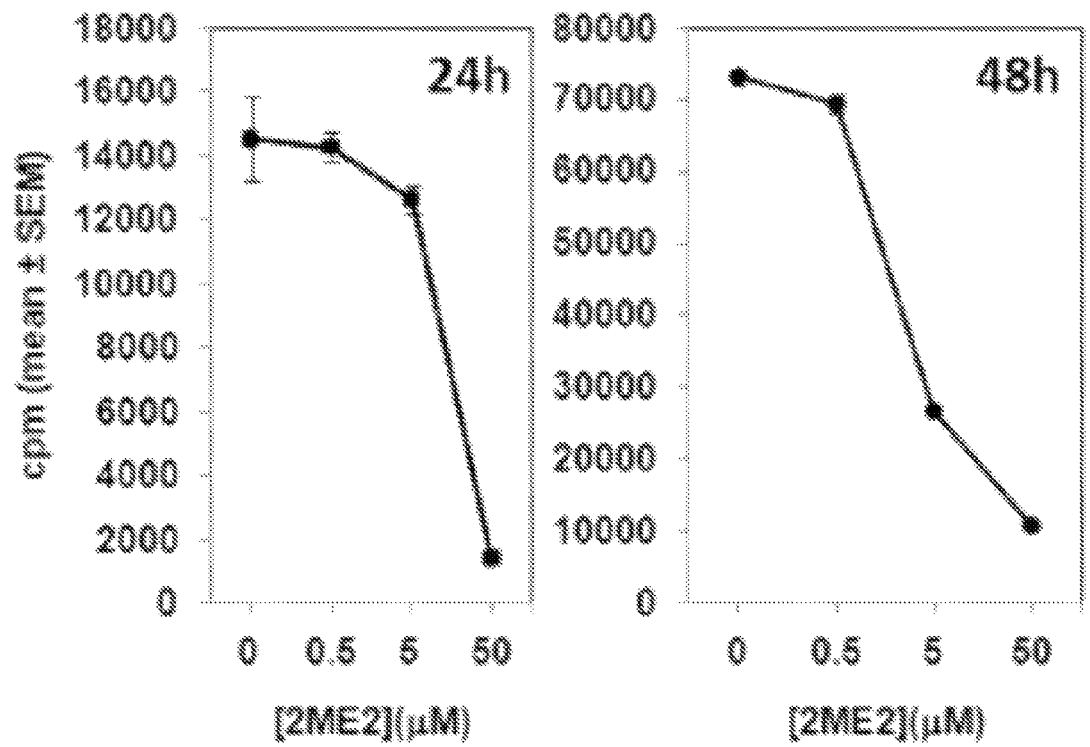

The effect of 2ME2 on proliferation of human T cells was examined in vitro. Stimulation of human PBL with anti-CD3/28 antibodies resulted in robust proliferation which was inhibited in a dose-dependent manner by 2ME2 (FIG. 2E). In addition, 2ME2 also inhibited anti-CD3/28-induced expression of CD25 on human PBL CD4$^+$ and CD8$^+$ T cells, as well as IL-17A, IFNγ and IL-2 production by CD3/28-stimulated human PBL. In summary, these results demonstrate that 2ME2 inhibits activation of lymphocytes in a dose dependent manner.

Figure 3A:
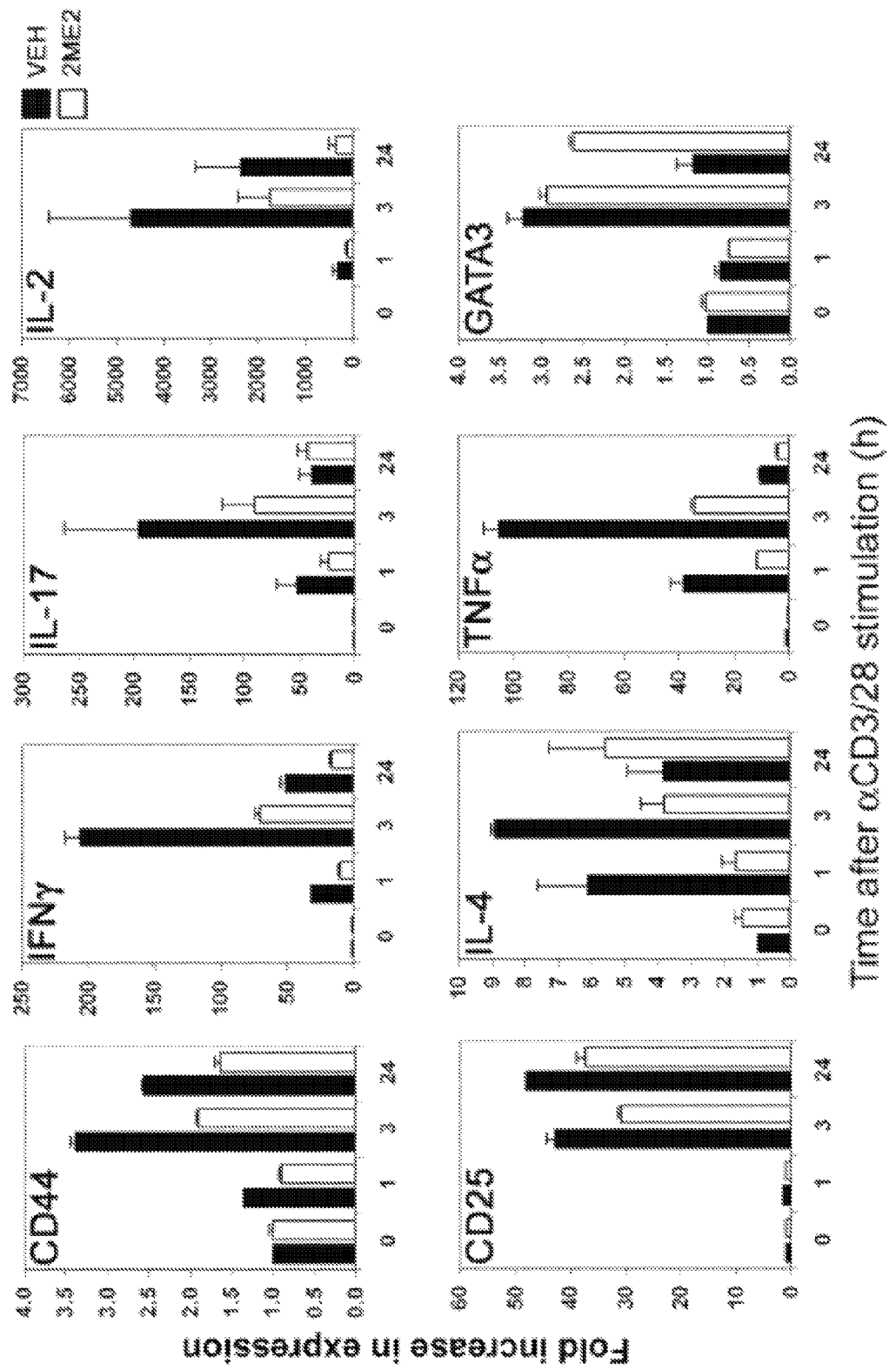
FIGS. 3A-3D show that 2ME2 treatment impairs cytokine production by activated T cells.
Figure 3B:
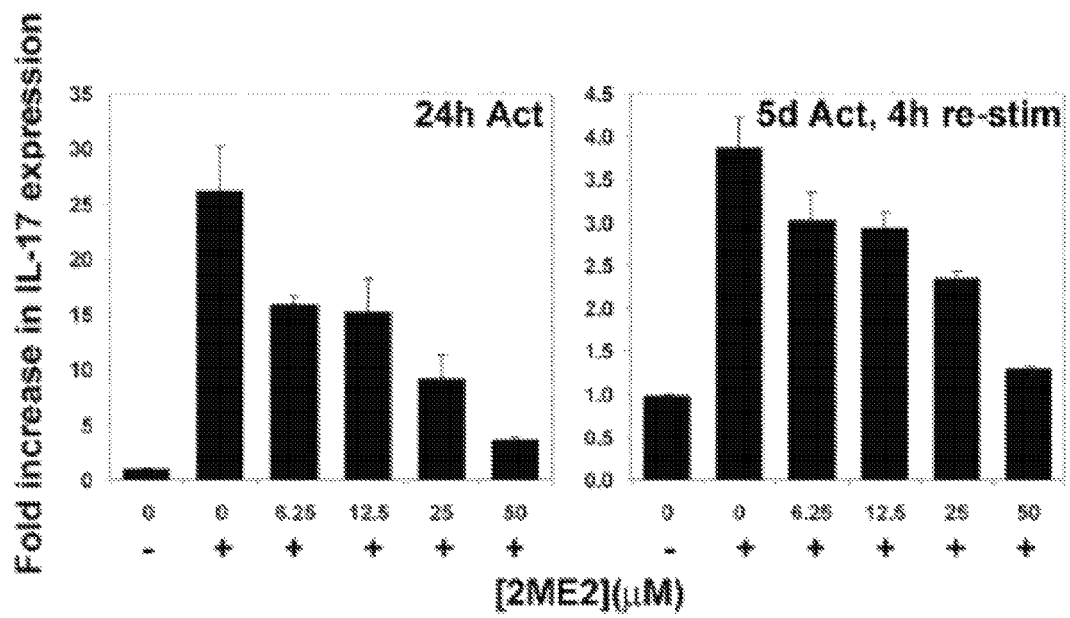

T cell cytokine expression is attenuated by 2ME2. Analysis of mRNA transcripts by quantitative real time (QRT) PCR revealed that 2ME2 decreased the induction of a range of cytokine and cell surface receptor mRNAs in activated T cells, including IL-2, TNFα, IFNγ, CD25 and CD44 (FIG. 3A). mRNA levels of the transcription factor GATA3, which is up-regulated via STAT6 activation, displayed normal induction 3 hours post stimulation. 2ME2's effects on IL-17 transcription were particularly dramatic, blocking up-regulation of IL-17 mRNA both after 3 hours anti-CD3/28 stimulation (FIG. 3A), and 24 hours (FIG. 3B, left). IL-17 production on re-stimulation after 5 days activation was also blocked by 2ME2 (FIG. 3B, right).

Figure 3C:
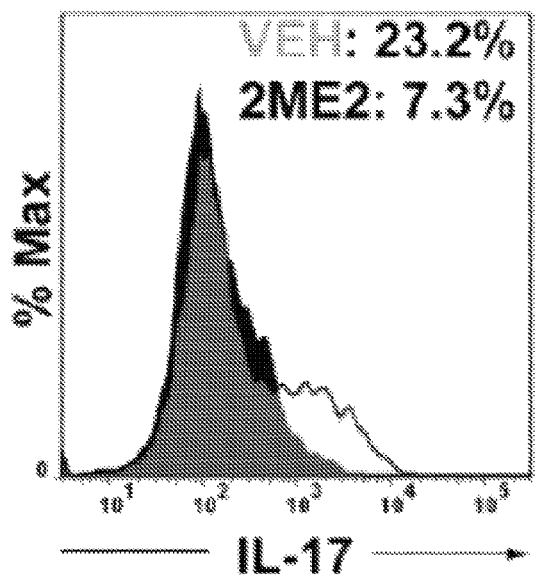

To address the effect of 2ME2 on Th17 cell function, naïve CD4$^+$ T cells were polarized into Th17 cells, pre-treated with vehicle or 2ME2, and subsequently re-stimulated with PMA/iono for 6 hours. While 23.2% of vehicle-treated Th17 cells stained positive for IL-17, only 7.3% of Th17 cells pretreated with 2ME2 were IL-17 positive (FIG. 3C). Production of IFNγ in these Th17 cells was not dramatically affected by 2ME2 treatment (9.1% vs. 7.3%, vehicle vs. control).

To assess whether 2ME2 modulated T cell cytokine production in vivo, mice were pre-treated with vehicle or 2ME2 for 2 days and subsequently injected them with 20 µg *Staphy-*

Figure 3D:
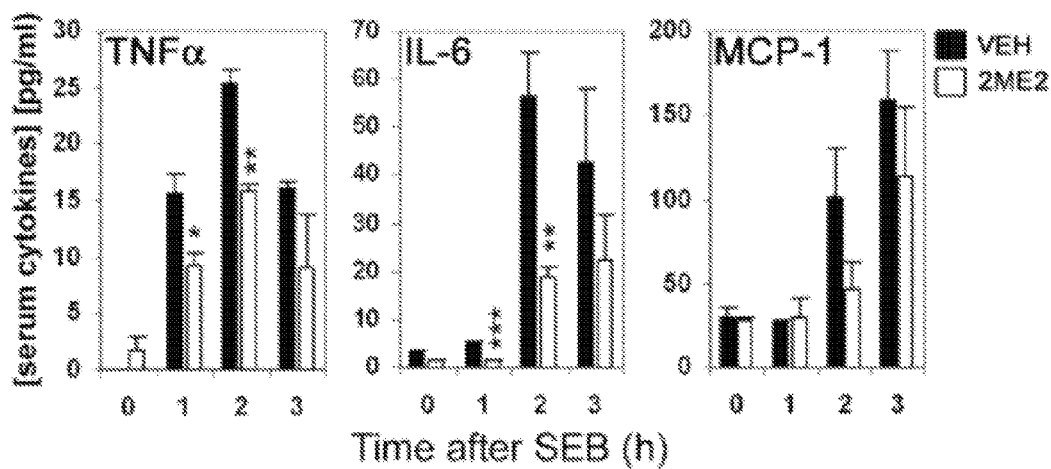

*lococcus* Enterotoxin B (SEB), which induces TCR-dependent pro-inflammatory cytokine production. 2ME2-treated mice produced significantly less serum TNFα and IL-6 than controls (FIG. 3D). These results show that 2ME2 reduces the production of inflammatory cytokines in vitro and in vivo.

Figure 6A:
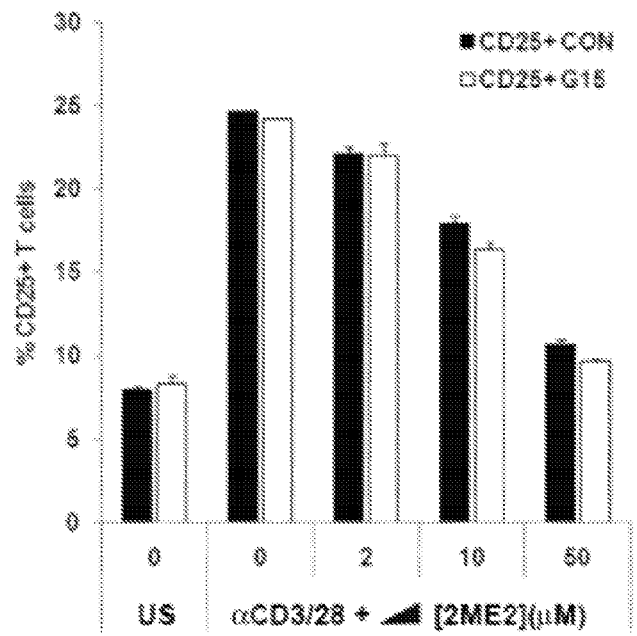
FIGS. 6A and 6B show purified CD4+ T cells that were pretreated with 2-50 µM 2ME2 and/or the GPER1 antagonist G15, and subsequently stimulated with anti-CD3/28 for 6 hours. Activation of CD4+ T cells was assessed by CD25 and CD69 upregulation, measured by flow cytometry. US, unstimulated. Data is shown as mean±SD for triplicate determinations, and is representative of two separate experiments.
Figure 6B:
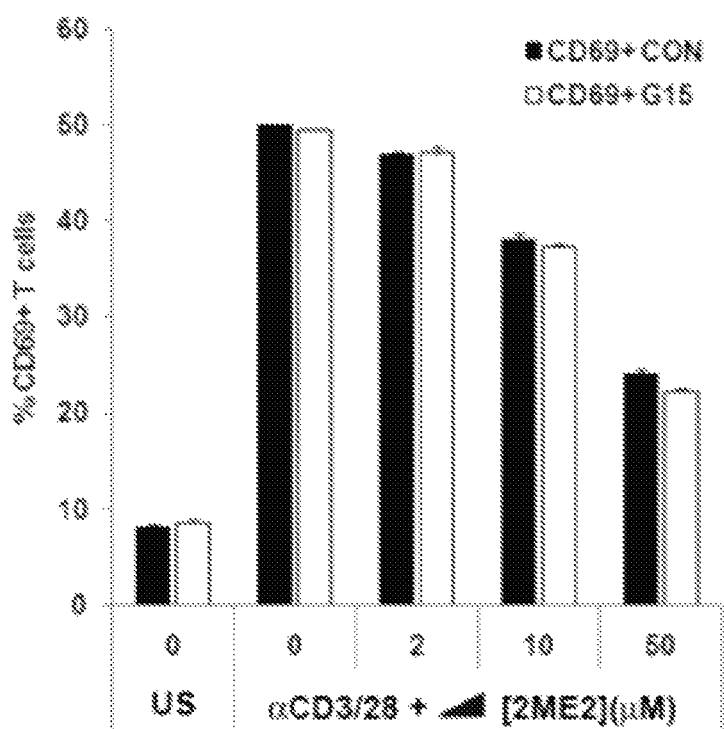

2ME2 inhibits NFAT activation, but has no effect on NF-κB or AP-1 signaling. Estrogens are known to confer protection against MS and EAE. Recent work has implicated the G protein-coupled estrogen receptor (GPER, also known as GPR30) 1 as a mediator of the protective role of 17-P estradiol in EAE. While 2ME2 exhibits poor affinity for the estrogen receptor (ER), exhibiting 500- and 3200-fold lower affinity than estradiol for ERα and ERβ respectively, its affinity for GPER1 has not been reported. Accordingly, the role of GPER1 signaling was determined in attenuation of T cell activation by 2ME2, using CD25 and CD69 expression 6 hours post activation as an indicator of inhibitory activity. To this end purified T cells were pre-incubated with 2ME2 and G15, a specific GPER1 antagonist, subsequently activating the cells with anti-CD3/28. Blockade of GPER1 with G15 failed to reverse the inhibitory effect of 2ME2 on CD25 expression (FIG. 6, top) or CD69 expression (FIG. 5, bottom) indicating that 2ME2 does not exert its modulatory effects on T cells through GPER1 activation. When the effect of G1, a specific agonist of GPER1, was tested on CD25 and CD69 expression on activated T cells, it was found that G1 had no effect on either parameter, supporting the fact that the mechanism of action of 2ME2 in T cells does not involve GPER1 signaling. Neither 2ME2, G1 nor G15 affected cell viability at 6 hours.

Figure 4A:
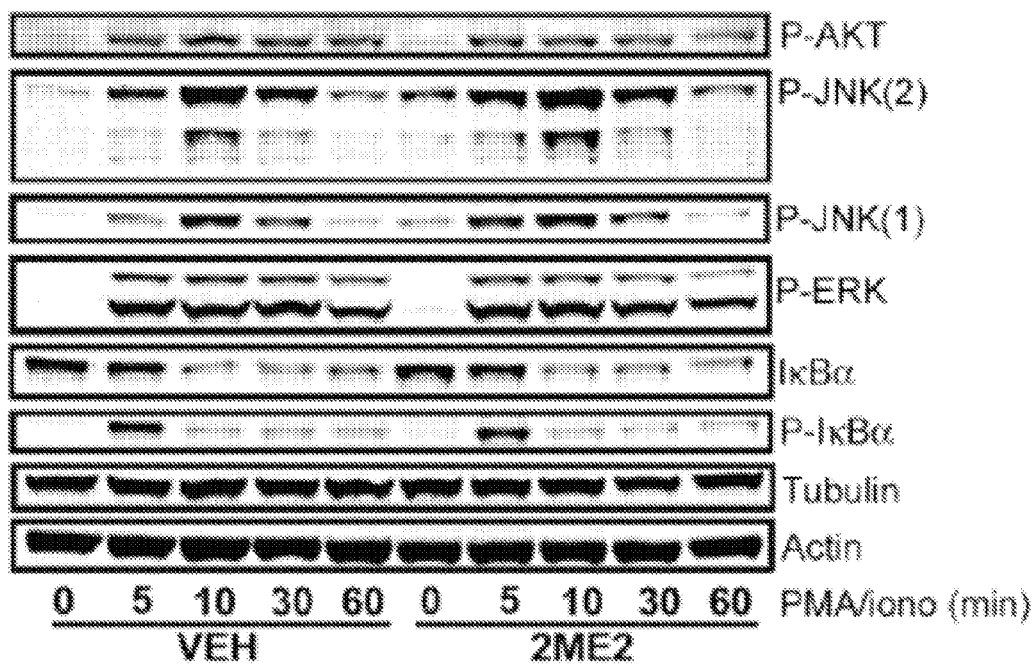
FIGS. 4A-4D show that 2ME2 disrupts NFAT signalling while leaving NF-κB signaling intact.
Figure 4B:
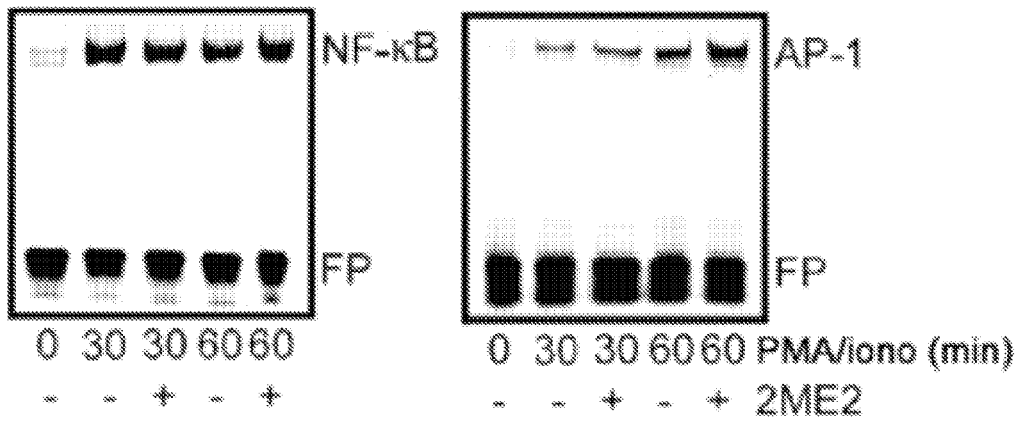

TCR ligation activates the transcription factor NF-κB, the MAPK pathway that triggers the AP-1 transcriptional complex, and the activation of NFAT. NFAT acts in concert with NF-κB and AP-1 to modulate the expression of genes critical for cellular activation and proliferation. To determine the effect of 2ME2 on these signaling pathways downstream of the TCR, T cells that had been pre-treated with vehicle or 2ME2 were stimulated with PMA/iono. IκBα phosphorylation and degradation were normal in 2ME2-treated activated T cells (FIG. 4A), as was the binding of NF-κB to DNA as assessed by EMSA (FIG. 4B). 2ME2 did not inhibit ERK or AKT phosphorylation, while the modest hyper-phosphorylation of JNK 1 and 2 present even in the absence of stimulation (FIG. 4A) presumably reflects the known activation of the stress kinase pathway by 2ME2. These data are consistent with the observation that 2ME2 induced a modest increase in AP-1 binding to DNA (FIG. 4B). In addition, 2ME2 did not inhibit NF-κB p65, JNK or ERK phosphorylation in T cells activated with anti-CD3/28. Thus, 2ME2 has no apparent inhibitory effect on the signaling mediators NF-κB, AP-1, ERK, AKT or JNK.

Figure 4C:
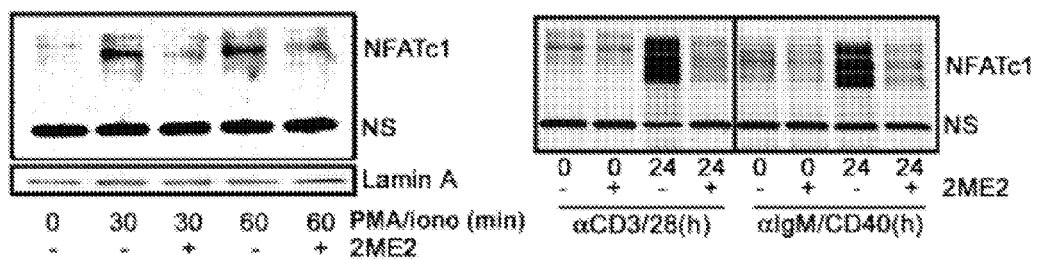
Figure 4D:
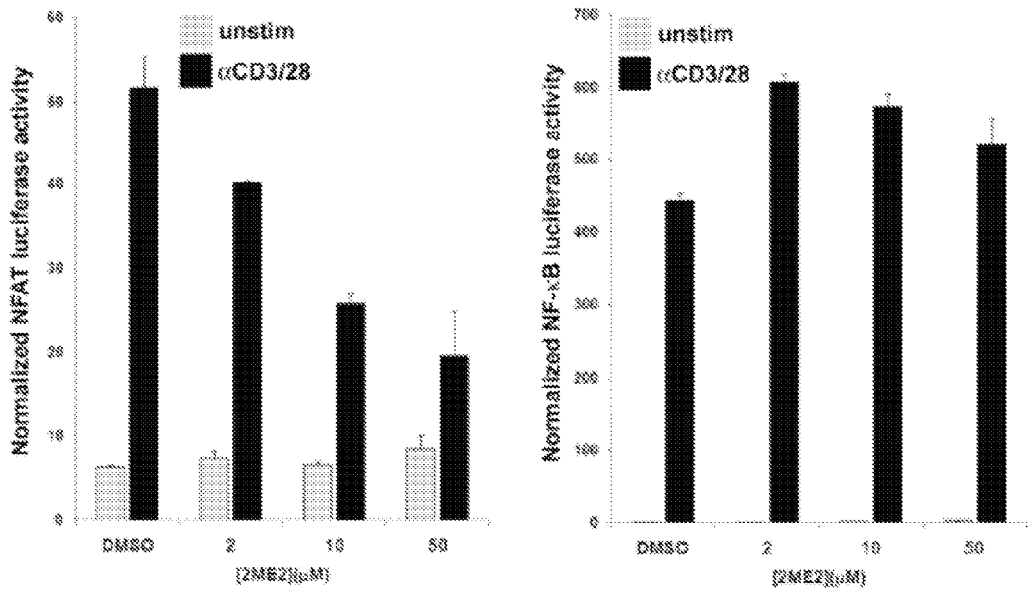

Pre-treatment with 2ME2 did however reduce the amount of NFATc1 present in the nuclear fraction of T cells at 30-60 minutes after PMA/iono stimulation (FIG. 4C, left), as well as in T cells and B cells 24 hours after anti-CD3/28 stimulation and anti-IgM/CD40-stimulation respectively (FIG. 4C, right). To confirm that 2ME2 caused a specific defect in NFAT activation Jurkat cell lines stably transfected with NFAT and NF-κB luciferase reporters were employed. Luciferase secretion was dependent on NFAT or NF-κB transcriptional activity, and was triggered via TCR activation with anti-CD3/28 antibodies (FIG. 4D). Addition of 2ME2 to these cultures prior to stimulation revealed that 2ME2 had no effect on NF-κB-dependent transcriptional activity; however transcriptional activation of NFAT via TCR ligation was dramatically inhibited by 2ME2 in a dose dependent fashion (FIG. 4D).

Together, the data presented herein indicate that 2ME2 blocks lymphocyte activation and proliferation by inhibiting NFATc1 nuclear translocation and NFAT-dependent gene transcription.

Discussion

The observation that exogenous 2ME2 induces cell cycle arrest and apoptosis in a variety of rapidly-dividing cells has led to the proposal that endogenous 2ME2 is a major mediator of the anti-mitogenic properties of estradiol. In vitro, 2ME2 potently inhibits endothelial cell proliferation and migration, and anti-angiogenic effects have been observed in several rodent tumor and non-tumor models. In addition to its anti-proliferative and anti-mitogenic effects, 2ME2 also appears to possess anti-inflammatory activity in mice, although the mechanism of action remains unclear.

The reported activity of 2ME2 in rodent CIA models prompted investigation of the efficacy of 2ME2 in EAE, which shares many key disease drivers with CIA, including Th17 cell development and pathogenic cytokine production. Interestingly, both RA and MS often enter remission during pregnancy, when serum and urine 2ME2 levels become highly elevated. The enzymes that convert estradiol to 2ME2 are ubiquitously expressed, and thus any tissue that is exposed to estradiol can produce 2ME2. It is therefore tempting to speculate that a rise in 2ME2 concentration in immune organs and/or the CNS may occur during pregnancy, and allow 2ME2 to reach concentrations necessary to produce disease modifying effects. While absorption of 2ME2 is reportedly efficient in mice and humans, low bioavailability is observed (1.5%), largely attributable to poor solubility and high first-pass metabolic transformation. Although it is difficult to achieve high serum 2ME2 concentrations following oral 2ME2 administration, the precise nature of local 2ME2 tissue accumulation and metabolism remains unclear, and it is possible that 2ME2 concentrations in local areas are significantly higher than those observed in serum. One approach to address the low solubility of 2ME2 has been the development of a NanoCrystal® Dispersion formulation of 2ME2 (Panzem NCD®), which increases bioavailability to 3-4%. Despite concerns related to bioavailability, orally-administered Panzem NCD® clearly exerts EAE disease-modifying activity in mice.

In order to elucidate the mechanism of action underlying this activity in EAE, it was determined whether 2ME2 affected signaling events immediately following antigen receptor TCR ligation in T cells. CD25 upregulation and production of IL-2 are both prerequisites for efficient T cell expansion in response to TCR stimulation and are (together with CD69 expression) dependent on NFAT nuclear translocation, and subsequent NFAT transcriptional activity. While NF-κB and MAPK pathways were unaffected by 2ME2 treatment, NFAT nuclear localization and transcriptional activity, together with CD25 and CD69 expression, were dose-dependently inhibited by 2ME2. In addition, as disclosed herein upregulation of mRNAs for the NFAT-dependent genes IL-2, IFNγ, IL-4, TNFα, CD25 and IL-17 that occurs in response to TCR ligation was inhibited by 2ME2-treatment. The ability of 2ME2 to inhibit Th17 cell IL-17 production may be particularly relevant to its disease-modifying role in EAE, IL-17 being a crucial encephalitogenic cytokine in the pathogenesis of EAE.

As demonstrated herein 2ME2 exerts its effects by impairing NFAT function in T cells as shown by in vivo experiments. In mice, SEB treatment induces TNFα production by T cells, leading to experimental toxic shock. As demonstrated herein pre-treatment of mice with 2ME2 significantly reduced the amount of TNFα and IL-6 produced by mice in response to SEB injection. In contrast, 2ME2-pretreated mice that were injected with LPS, which causes experimental septic shock, showed no reduction in serum TNFα levels SEB-induced TNFα production by T cells depends on NFATc2, whereas LPS-induced TNFα production is attributable largely to macrophages and depends on TLR4 signaling, and is not $Ca^{2+}$ dependent. These results are thus consistent with a previous report showing that NFATc2-deficient mice are not susceptible to toxic shock, but retain sensitivity to LPS injection. Taken together, these data indicate that disruption of NFAT activity is largely responsible for the inhibitory effects of 2ME2 on lymphocytes in vitro and on EAE progression in vivo.

In conclusion, the studies presented herein provides the first evidence that 2ME2 reduces NFAT activity specifically. This impairment compromises the activation and proliferation of lymphocytes, and may underlie the disease-modifying activity of 2ME2 in both RA and EAE. Our promising EAE data in mice, together with favorable preclinical results and safety data obtained from oncology patients, strongly indicate that oral 2ME2 may be a well-tolerated, safe and convenient alternative to current biologic and small molecule drugs used in the treatment of autoimmune disorders such as MS.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

What is claimed is:

1. A method of inhibiting or reducing lymphocyte activation and proliferation in a subject undergoing autoimmune demyelination, which comprises administering to the subject a therapeutically effective amount of a 2ME2 compound having the following formula:

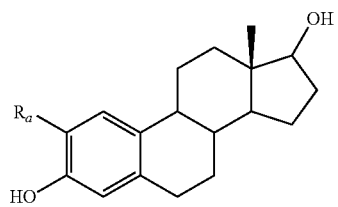

wherein $R_a$ is selected from the group consisting of —OCH$_3$, —OCH$_2$CH$_3$, —CH$_3$, —CH$_2$CH$_3$, —CCCH$_3$, —CHCH—CH$_3$, and —CH$_2$—CHCH$_2$.

2. The method of claim 1, which further comprises administering to the subject a second agent selected from the group consisting of a steroid, an anti-inflammatory compound, an immunosuppressive compound, and an antioxidant.

3. The method of claim 2, wherein the second agent is beta-interferon.

4. The method of claim 2, wherein the second agent is glatiramer acetate.

5. The method of claim 2, wherein the second agent is lipoic acid.

6. The method of claim 2, wherein the second agent is a monoclonal antibody.

7. The method of claim 2, wherein the second agent is selected from the group consisting of daclizumab, rituximab, and natalizumab.

8. The method of claim 2, wherein the second agent is sanglifehrin A or a compound having cyclophilin D inhibitory activity.

9. The method of claim 1, wherein administration of the 2ME2 compound is oral, parenteral, transdermal, topical, intravenous, subcutaneous, intramuscular, intradermal, ophthalmic, epidural, intratracheal, sublingual, buccal, rectal, vaginal, nasal, or inhalation.

10. A method of inhibiting or reducing NFATc1 nuclear translocation and NFAT-dependent gene transcription in a subject undergoing autoimmune demyelination, which comprises administering to the subject a therapeutically effective amount of a 2ME2 compound having the following formula:

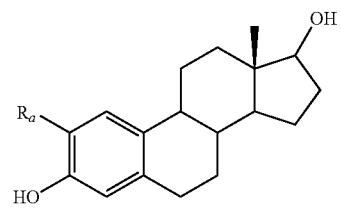

wherein $R_a$ is selected from the group consisting of —OCH$_3$, —OCH$_2$CH$_3$, —CH$_3$, —CH$_2$CH$_3$, —CCCH$_3$, —CHCH—CH$_3$, and —CH$_2$—CHCH$_2$.

11. The method of claim 10, which further comprises administering to the subject a second agent selected from the group consisting of a steroid, an anti-inflammatory compound, an immunosuppressive compound, and an antioxidant.

12. The method of claim 11, wherein the second agent is beta-interferon.

13. The method of claim 11, wherein the second agent is glatiramer acetate.

14. The method of claim 11, wherein the second agent is lipoic acid.

15. The method of claim 11, wherein the second agent is a monoclonal antibody.

16. The method of claim 11, wherein the second agent is selected from the group consisting of daclizumab, rituximab, and natalizumab.

17. The method of claim 11, wherein the second agent is sanglifehrin A or a compound having cyclophilin D inhibitory activity.

18. The method of claim 10, wherein administration of the 2ME2 compound is oral, parenteral, transdermal, topical, intravenous, subcutaneous, intramuscular, intradermal, ophthalmic, epidural, intratracheal, sublingual, buccal, rectal, vaginal, nasal, or inhalation.

19. A method of inhibiting or reducing T cell cytokine production in a subject undergoing autoimmune demyelination, which comprises administering to the subject a thera peutically effective amount of a 2ME2 compound having the following formula:

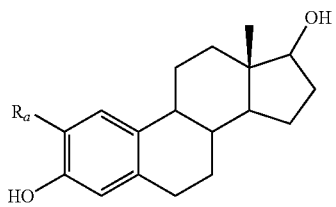

wherein $R_a$ is selected from the group consisting of —OCH$_3$, —OCH$_2$CH$_3$, —CH$_3$, —CH$_2$CH$_3$, —CCCH$_3$, —CHCH—CH$_3$, and —CH$_2$—CHCH$_2$.

20. The method of claim 19, which further comprises administering to the subject a second agent selected from the group consisting of a steroid, an anti-inflammatory compound, an immunosuppressive compound, and an antioxidant.

21. The method of claim 20, wherein the second agent is beta-interferon.

22. The method of claim 20, wherein the second agent is glatiramer acetate.

23. The method of claim 20, wherein the second agent is lipoic acid.

24. The method of claim 20, wherein the second agent is a monoclonal antibody.

25. The method of claim 20, wherein the second agent is selected from the group consisting of daclizumab, rituximab, and natalizumab.

26. The method of claim 20, wherein the second agent is sanglifehrin A or a compound having cyclophilin D inhibitory activity.

27. The method of claim 19, wherein administration of the 2ME2 compound is oral, parenteral, transdermal, topical, intravenous, subcutaneous, intramuscular, intradermal, ophthalmic, epidural, intratracheal, sublingual, buccal, rectal, vaginal, nasal, or inhalation.

* * * * *